(12) United States Patent
Kume et al.

(10) Patent No.: US 10,457,916 B2
(45) Date of Patent: Oct. 29, 2019

(54) METHOD FOR INDUCING DIFFERENTIATION OF INSULIN-PRODUCING CELLS

(71) Applicant: TOKYO INSTITUTE OF TECHNOLOGY, Tokyo (JP)

(72) Inventors: Shoen Kume, Tokyo (JP); Nobuaki Shiraki, Tokyo (JP)

(73) Assignee: Tokyo Institute of Technology, Tokyo (JP)

( * ) Notice: Subject to any disclaimer, the term of this patent is extended or adjusted under 35 U.S.C. 154(b) by 0 days.

(21) Appl. No.: 15/312,273

(22) PCT Filed: May 19, 2015

(86) PCT No.: PCT/JP2015/064380
§ 371 (c)(1),
(2) Date: Nov. 18, 2016

(87) PCT Pub. No.: WO2015/178397
PCT Pub. Date: Nov. 26, 2015

(65) Prior Publication Data
US 2017/0081639 A1  Mar. 23, 2017

(30) Foreign Application Priority Data

May 20, 2014  (JP) .................. 2014-104019

(51) Int. Cl.
| | |
|---|---|
| *C12N 5/071* | (2010.01) |
| *A61K 35/12* | (2015.01) |
| *G01N 33/50* | (2006.01) |
| *G01N 33/74* | (2006.01) |
| *C12N 15/09* | (2006.01) |

(52) U.S. Cl.
CPC ............ *C12N 5/0676* (2013.01); *A61K 35/12* (2013.01); *C12N 5/0678* (2013.01); *G01N 33/507* (2013.01); *G01N 33/5073* (2013.01); *G01N 33/74* (2013.01); *C12N 15/09* (2013.01); *C12N 2500/92* (2013.01); *C12N 2500/98* (2013.01); *C12N 2501/01* (2013.01); *C12N 2501/119* (2013.01); *C12N 2501/15* (2013.01); *C12N 2501/155* (2013.01); *C12N 2501/16* (2013.01); *C12N 2501/385* (2013.01); *C12N 2501/41* (2013.01); *C12N 2501/415* (2013.01); *C12N 2501/727* (2013.01); *C12N 2501/73* (2013.01); *C12N 2506/45* (2013.01); *C12N 2533/52* (2013.01)

(58) Field of Classification Search
CPC ................................................... C12N 5/0676
See application file for complete search history.

(56) References Cited

U.S. PATENT DOCUMENTS

| | | | |
|---|---|---|---|
| 2009/0170198 A1* | 7/2009 | Rezania | ............... C12N 5/0676 435/377 |
| 2010/0015100 A1 | 1/2010 | Xu | |
| 2015/0140661 A1 | 5/2015 | Toyoshima et al. | |

FOREIGN PATENT DOCUMENTS

| | | |
|---|---|---|
| EP | 2505639 A1 | 10/2012 |
| EP | 2857500 A1 | 4/2015 |
| JP | 2009-225661 A | 10/2009 |
| JP | 2010-535036 A | 11/2010 |
| WO | WO 03/046141 A2 | 6/2003 |
| WO | WO 2009/070592 A2 | 6/2009 |
| WO | WO 2013/095953 A1 | 6/2013 |
| WO | WO 2013/176249 A1 | 11/2013 |

OTHER PUBLICATIONS

D'Amour et al. (2006, Nature Biotechnology, vol. 24(11), pp. 1392-1401) (Year: 2006).*
Kelly et al. (2009, Nature Biotechnology, vol. 29(8), pp. 750-758 + Supplemental Data, pp. 1-10) (Year: 2009).*
Thatava et al. (2011, Gene Therapy, vol. 18, pp. 283-293). (Year: 2011).*
NIH Stem Cells—11 Pages (Year: 2016).*
International Search Report (PCT/ISA/210) issued in PCT/JP2015/064380, dated Aug. 18, 2015.

(Continued)

*Primary Examiner* — Thaian N Ton
*Assistant Examiner* — David A. Montanari
(74) *Attorney, Agent, or Firm* — Morgan, Lewis & Bockius LLP

(57) ABSTRACT

It is an object of the present invention to provide a method for efficiently directing differentiation into insulin-producing cells in a xeno-free culture system. According to the present invention, there is provided a method for directed differentiation into insulin-producing cells, comprising culturing stem cells in the following steps (1) to (5): (1) a step of culturing stem cells in a medium comprising an activator of activin receptor-like kinase-4/-7 and a GSK3 inhibitor and then culturing in a medium comprising an activator of activin receptor-like kinase-4/-7; (2) a step of culturing the cells obtained in step (1) in a medium comprising a hedgehog signaling inhibitor and an FGF; (3) a step of culturing the cells obtained in step (2) in a medium comprising a retinoic acid receptor agonist, a hedgehog signaling inhibitor and a BMP signaling inhibitor; (4) a step of culturing the cells obtained in step (3) in a medium comprising a TGF-β type I activin receptor-like kinase-4/-5/-7 inhibitor and a BMP signaling inhibitor; and (5) a step of culturing the cells obtained in step (4) in a medium comprising a phosphodiesterase inhibitor.

22 Claims, 15 Drawing Sheets

Specification includes a Sequence Listing.

(56) References Cited

OTHER PUBLICATIONS

Sakano et al., "VMAT2 identified as a regulator of late-stage β-cell differentiation", Nature Chemical Biology, vol. 10, pp. 141-148, Dec. 15, 2013, 34 pages, including online additional matterials.
Shiraki et al., "Pancreatic, hepatic and intestinal differentiation of ES/iPS cells", Journal of Clinical and Experimental Medicine, vol. 251, Nos. 12, 13, Dec. 27, 2014, pp. 1153-1159.
Written Opinion (PCT/ISA/237) issued in PCT/JP2015/064380, dated Aug. 18, 2015.
English translation of International Preliminary Report on Patentability dated Nov. 24, 2016, in PCT International Application No. PCT/JP2015/064380.
Extended European Search Report, dated Jan. 22, 2018, for European Application No. 15795718.4.
Shahjalal et al., "Generation of Insulin-producing β-like Cells from Human iPS Cells in a Defined and Completely Xeno-free Culture System," Journal of Molecular Cell Biology Advance Access, vol. 6, No. 5, Jun. 24, 2014 (Electronically available Jul. 3, 2014), pp. 1-15, XP055278811.

* cited by examiner

METHOD FOR INDUCING DIFFERENTIATION OF INSULIN-PRODUCING CELLS

TECHNICAL FIELD

The present invention relates to a method for directed differentiation into insulin-producing cells in a xeno-free culture system. Further, the present invention relates to insulin-producing cells obtained by the above method, pharmaceuticals using the same, and a method of screening for medicines using the same.

BACKGROUND ART

Diabetes is a life-long disease characterized by chronic hyperglycemia. Type 1 diabetes is caused by autoimmune destruction of insulin producing β-cells in the pancreas and its treatment is solely dependent on insulin administration. Islet transplantation from cadaveric donors is a promising therapy for type 1 diabetes; however, due to difficulties of obtaining transplantable islets from cadaveric pancreas, alternative cell sources for the generation of insulin expressing β-cells are expected.

Human pluripotent stem cells, e.g., human embryonic stem (hES) cells and human induced pluripotent stem (hiPS) cells, possess the capacity for unlimited replication and the potential to differentiate into all major somatic cell lineages. Therefore, it is believed that those cells are a potential material for generating insulin-producing, pancreatic β-cells. Further, those cells have great potential for use in cell-based therapy and drug discovery. Many studies reported the generation of pancreatic endocrine cells from human ES/iPS cells in various in vitro feeder-cell culture systems (Non-Patent Documents Nos. 1-4) or feeder-free culture systems (Non-Patent Documents Nos. 5-9). Studies on the differentiation of human ES or iPS cells into endodermal or pancreatic cell lineages have shown that activin, fibroblast growth factor (FGF), stimulation with retinoic acid (RA), and inhibition of signaling of hedgehog, bone morphogenetic protein (BMP) and transforming growth factor (TGF)-β promote the differentiation into endodermal or pancreatic lineages (Non-Patent Documents Nos. 1-5 and 10). Stepwise differentiation protocols have been designed to mimic pancreatic differentiation and to successfully generate insulin-expressing cells from human ES or iPS cells.

However, pancreatic β-like cells generated to date from human ES/iPS cells in vitro are largely polyhormonal and exhibit limited capacity of glucose-stimulated insulin secretion (GSIS), a characteristic of functionally mature β-cells (Non-Patent Documents Nos. 6, 8, 10 and 11; Patent Documents Nos. 1 and 2). Moreover, use of chemically undefined raw materials in the generation of β-cells may cause problems in clinical applications in the future. Therefore, development of a method for generating functional and yet terminally differentiated endocrine cell-type β-cells from human iPS (hiPS) cells in a defined xeno-free culture system has been greatly desired.

PRIOR ART LITERATURE

Patent Documents

Patent Document No. 1: Japanese Unexamined Patent Publication (Translation of PCT Application) No. 2011-0811222

Patent Document No. 2: Japanese Unexamined Patent Publication (Translation of PCT Application) No. 2013-515480

Non-Patent Documents

Non-Patent Document No. 1: Kunisada et al., Stem Cell Res 2012; 8:274-284
Non-Patent Document No. 2: Chen et al., Nat Chem Biol 2009; 5:258-265
Non-Patent Document No. 3: Kroon et al., Nat Biotechnol 2008; 26: 443-452
Non-Patent Document No. 4: D'Amour et al., Nat Biotechnol 2006; 24:1392-1401
Non-Patent Document No. 5: Rezania et al., Diabetes 2012; 61: 2016-2029
Non-Patent Document No. 6: Zhang et al., Cell Res 2009; 19:429-438
Non-Patent Document No. 7: Jiang et al., Cell Res 2007; 17:333-344
Non-Patent Document No. 8: Jiang et al., Stem Cells 2007; 25:1940-1953
Non-Patent Document No. 9: Shi et al., Stem Cells 2005; 23:656-662
Non-Patent Document No. 10: Mfopou et al., Gastroenterology 2010; 138:2233-2245
Non-Patent Document No. 11: Shiraki et al., Genes Cells 13, 731-746. (2008)
Non-Patent Document No. 12: Martin et al., Nat Med 2005; 11:228-232

DISCLOSURE OF THE INVENTION

Problem for Solution by the Invention

It is an object of the present invention to provide a method for efficiently directing differentiation into insulin-producing cells in a xeno-free culture system. Specifically, the present invention aims at more efficiently directing stem cells (such as human ES cells or iPS cells) to differentiate into pancreatic β-like cells to thereby generate functional insulin-producing cells stably. Further, it is another object of the present invention to provide pharmaceuticals comprising insulin-producing cells obtained by the method of the present invention and a method of screening for medicines using such cells.

Means to Solve the Problem

As a result of intensive and extensive researches toward solution of the above-described problems, the present inventors have found that it is possible to direct stem cells to differentiate into insulin-producing cells more efficiently by changing the types and combinations of differentiation-inducing factors in a stepwise manner. Thus, the present invention has been achieved. More specifically, the present inventors have found that cooperative action of NOGGIN and IBMX more efficiently directs stem cells to differentiate into functionally mature insulin-producing cells that secret C-peptide in response to insulin secretion accelerator and hyperglycemia. Thus, the present invention has been achieved. As one embodiment of the present invention, there is provided a 5-step xeno-free culture system which efficiently directs hiPS cells to differentiate into insulin-producing cells in vitro.

The present invention provides the following inventions.

[1] A method for directed differentiation into insulin-producing cells, comprising culturing stem cells in the following steps (1) to (5):

(1) a step of (1-1) culturing stem cells in a medium comprising an activator of activin receptor-like kinase-4/-7 and a GSK3 inhibitor and then (1-2) culturing in a medium comprising an activator of activin receptor-like kinase-4/-7;

(2) a step of culturing the cells obtained in step (1) in a medium comprising a hedgehog signaling inhibitor and an FGF;

(3) a step of culturing the cells obtained in step (2) in a medium comprising a retinoic acid receptor agonist, a hedgehog signaling inhibitor and a BMP signaling inhibitor (preferably, further comprising a TGF-β type I activin receptor-like kinase-4/-5/-7 inhibitor);

(4) a step of culturing the cells obtained in step (3) in a medium comprising a TGF-β type I activin receptor-like kinase-4/-5/-7 inhibitor and a BMP signaling inhibitor (preferably, further comprising a protein kinase C activator); and (5) a step of culturing the cells obtained in step (4) in a medium comprising a phosphodiesterase inhibitor (preferably, further comprising one or more members, preferably two or more members, or especially preferably all members of the group consisting of a GLP-1 receptor agonist, nicotinamide and an adenylate cyclase activator).

[2] The method of [1] above, wherein the medium in step (1-2) does not substantially comprise a GSK3 inhibitor.

[3] The method of [1] or [2] above, wherein the BMP signaling inhibitor in steps (3) and (4) is NOGGIN and the phosphodiesterase inhibitor in step (5) is IBMX.

[4] The method of [3] above, wherein the concentration of NOGGIN in steps (3) and (4) is at least 100 ng/ml or more.

[5] The method of [4] above, wherein the concentration of NOGGIN in steps (3) and (4) is at least 200-500 ng/ml.

[6] The method of any one of [1] to [5] above, wherein step (3) comprises a retinoic acid receptor agonist, a hedgehog signaling inhibitor, a BMP signaling inhibitor and a TGF-β type I activin receptor-like kinase-4/-5/-7 inhibitor; step (4) comprises a TGF-β type I activin receptor-like kinase-4/-5/-7 inhibitor, a BMP signaling inhibitor and a protein kinase C activator; and step (5) comprises a phosphodiesterase inhibitor, a GLP-1 receptor agonist, nicotinamide and an adenylate cyclase activator.

[7] The method of any one of [1] to [6] above, wherein the retinoic acid receptor agonist in step (3) is retinoic acid and the hedgehog signaling inhibitor in steps (2) and (3) is KAAD-cyclopamine.

[8] The method of [6] or [7] above, wherein the TGF-β type I activin receptor-like kinase-4/-5/-7 inhibitor in step (3) is SB431542 and the GLP-1 receptor agonist in step (5) is exendin-4.

[9] The method of any one of [1] to [8] above, which is characterized by conducting all of the steps (1) to (5) in a xeno-free culture system.

[10] A method for directed differentiation into insulin-producing cells, comprising culturing stem cell-derived endodermal cells in the following steps (a) to (d):

(a) a step of culturing the endodermal cells in a medium comprising a hedgehog signaling inhibitor and an FGF;

(b) a step of culturing the cells obtained in step (a) in a medium comprising a retinoic acid receptor agonist, a hedgehog signaling inhibitor and a BMP signaling inhibitor (preferably, further comprising a TGF-β type I activin receptor-like kinase-4/-5/-7 inhibitor);

(c) a step of culturing the cells obtained in step (b) in a medium comprising a TGF-β type I activin receptor-like kinase-4/-5/-7 inhibitor and a BMP signaling inhibitor (preferably, further comprising a protein kinase C activator); and (d) a step of culturing the cells obtained in step (c) in a medium comprising a phosphodiesterase inhibitor (preferably, further comprising one or more members, preferably two or more members, or especially preferably all members of the group consisting of a GLP-1 receptor agonist, nicotinamide and an adenylate cyclase activator).

[11] The method of [10] above, wherein the BMP signaling inhibitor in steps (b) and (c) is NOGGIN and the phosphodiesterase inhibitor in step (d) is IBMX.

[12] The method of [11] above, wherein the concentration of NOGGIN in steps (b) and (c) is at least 100 ng/ml or more.

[13] The method of [12] above, wherein the concentration of NOGGIN in steps (c) and (d) is 200-500 ng/ml.

[14] The method of any one of [10] to [13] above, wherein step (b) comprises a retinoic acid receptor agonist, a hedgehog signaling inhibitor, a BMP signaling inhibitor and a TGF-β type I activin receptor-like kinase-4/-5/-7 inhibitor; step (c) comprises a TGF-β type I activin receptor-like kinase-4/-5/-7 inhibitor, a BMP signaling inhibitor and a protein kinase C activator; and step (d) comprises a phosphodiesterase inhibitor, a GLP-1 receptor agonist, nicotinamide and an adenylate cyclase activator.

[15] The method of any one of [10] to [14] above, wherein the retinoic acid receptor agonist in step (b) is retinoic acid and the hedgehog signaling inhibitor in steps (a) and (b) is KAAD-cyclopamine.

[16] The method of [14] or [15] above, wherein the TGF-β type I activin receptor-like kinase-4/-5/-7 inhibitor in step (b) is SB431542 and the GLP-1 receptor agonist in step (d) is exendin-4.

[17] The method of any one of [10] to [16] above, which is characterized by conducting all of the steps (a) to (d) in a xeno-free culture system.

[18] The method of any one of [1] to [17] above, wherein the stem cell is induced pluripotent stem cells (iPS cells), embryonic stem cells (ES cells) or human somatic stem cells.

[19] Insulin-producing cells obtained by the method of any one of [1] to [18] above.

[20] A pharmaceutical composition comprising the cells of [19] above.

[21] A method of screening for therapeutics for diabetes, comprising using insulin-producing cells obtained by the method of any one of [1] to [18] above.

[22] The method of [21] above, comprising a step of culturing the insulin-producing cells with a subject substance.

[23] The method of [22] above, further comprising a step of detecting insulin secretion by the cells.

Effect of the Invention

According to the present invention, it is possible to direct stem cells to differentiate into insulin-producing cells more efficiently. The insulin-producing cells obtained by the method of directed differentiation of the present invention may be used for screening for those compounds useful for prevention and/or treatment of diseases such as diabetes. Further, the insulin-producing cells obtained by the method of directed differentiation of the present invention may be used in cell-based therapy for treating diseases such as diabetes.

BEST MODES FOR CARRYING OUT THE INVENTION

Figure 1:
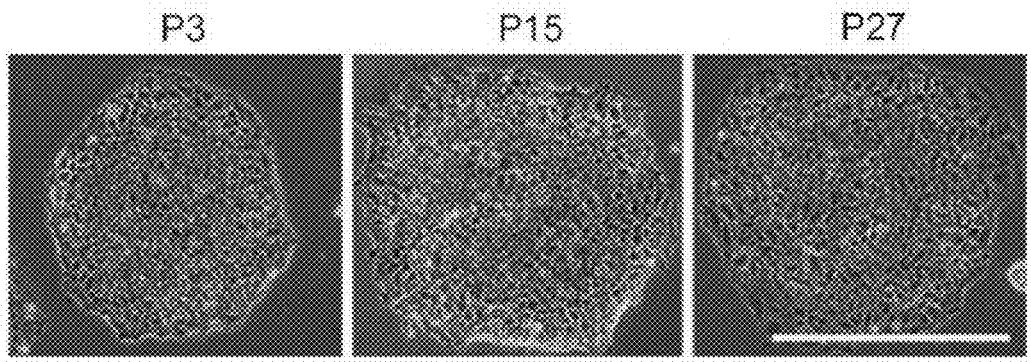
FIG. 1 Photographs showing morphologies of undifferentiated hiPS cells passaged under xeno-free conditions are presented. P3, P15 and P27 show individual morphologies after 3 passages, 15 passages and 27 passages, respectively. Scale bar=1 mm.

Hereinbelow, the present invention will be described in detail. However, the present invention is not limited to the embodiments described below.

The terms used in the present specification have meanings conventionally used in the field of the relevant art unless otherwise indicated specifically. It should be noted here that the expression "A to B" is used herein, the expression is intended to include A as the lower limit and B as the upper limit.

The term "insulin-producing cells" used herein mean cells that secret insulin in response to insulin secretagogues and hyperglycemia and have a significantly superior capacity of insulin expression compared with expression capacities for other pancreatic hormones. As other pancreatic hormones, glucagon, somatostatin or the like may be given.

When the term "prepare" or "generate" is used herein intending to prepare insulin-producing cells, such a term may be replaced with "differentiate into (direct differentiation into)". Unless otherwise noted, these terms are used exchangeably.

The term "pluripotent stem cells" used herein refers to cells that have replication competence, are capable of cultivation in vitro, and have pluripotency that enables differentiation into cells constituting individuals. Specific examples of pluripotent stem cells include, but are not limited to, embryonic stem cells (ES cells), fetal primordial germ cell-derived pluripotent stem cells (GS cells), somatic cell-derived induced pluripotent stem cells (iPS cells) and somatic stem cells. In the present invention, iPS or ES cells are preferably used. Particularly preferable are human iPS cells and human ES cells.

ES cells may be mammal-derived ES cells; the type and the method of acquisition are not particularly limited. As the mammal, mouse, rat, guinea pig, hamster, rabbit, cat, dog, sheep, cattle, horse, goat, monkey or human may be enumerated, for example. Preferably, mouse or human may be enumerated. More preferably, human is given.

Generally, ES cells may be established as a cell strain ultimately by culturing fertilized eggs of blastocyst stage with feeder cells, breaking up the resultant grown up internal cell mass-derived cells, and repeating passage operations. Thus, ES cells are largely obtained from fertilized eggs. Alternatively, it is possible to obtain ES cells from other than fertilized eggs, e.g., lipid tissue, placenta, testis cells, or the like. Any of these ES cells are objects of the present invention.

Further, iPS cells (induced pluripotent stem cells) refers to cells which have acquired pluripotency. More specifically, cells which have acquired pluripotency equivalent to that of ES cells by introduction of several types of transcription factor (pluripotency factor) genes into somatic cells (such as fibloblasts). As "pluripotency factors", a large number of factors have been reported. Specific examples of pluripotency factors include, but are not limited to, Oct family (e.g., Oct 3/4), Sox family (e.g., Sox2, Sox1, Sox3, Sox15 and Sox 17), Klf family (e.g., Klf 4 and Klf2), Myc family (e.g., c-Myc, N-Myc and L-Myc), Nanog and LIN28. With respect to methods for establishing iPS cells, a number of reports have been made and can be consulted with (for example, Takahashi et al., Cell 2006, 126:663-676; Okita et al., Nature 2007, 448:313-317; Wernig et al., Nature 2007, 448:318-324; Maherali et al., Cell Stem Cell 2007, 1:55-70; Park et al., Nature 2007, 451:141-146; Nakagawa et al, Nat Biotechnol 2008, 26:101-106; Wernig et al., Cell Stem Cell 2008, 10:10-12; Yu et el., Science 2007, 318:1917-1920; Takahashi et al., Cell 2007, 131:861-872; and Stadtfeld et al., Science 2008 322:945-949).

1. Method for Directed Differentiation into Insulin-Producing Cells

The method for directed differentiation of the present invention is a method of directing stem cells to differentiate into insulin-producing cells. The method for directed differentiation of the present invention is also a method of directing endodermal cells, primitive gut tube cells or pancreatic progenitor cells to differentiate into insulin-producing cells.

The present invention relates to a method for directed differentiation into insulin-producing cells, comprising culturing stem cells in the following steps (1) to (5):

(1) a step of (1-1) culturing stem cells in a medium comprising an activator of activin receptor-like kinase-4/-7 and a GSK3 inhibitor and then (1-2) culturing in a medium comprising an activator of activin receptor-like kinase-4/-7;

(2) a step of culturing the cells obtained in step (1) in a medium comprising a hedgehog signaling inhibitor and an FGF;

(3) a step of culturing the cells obtained in step (2) in a medium comprising a retinoic acid receptor agonist, a hedgehog signaling inhibitor and a BMP signaling inhibitor (preferably, further comprising a TGF-β type I activin receptor-like kinase-4/-5/-7 inhibitor);

(4) a step of culturing the cells obtained in step (3) in a medium comprising a TGF-β type I activin receptor-like kinase-4/-5/-7 inhibitor and a BMP signaling inhibitor (preferably, further comprising a protein kinase C activator); and (5) a step of culturing the cells obtained in step (4) in a medium comprising a phosphodiesterase inhibitor (preferably, further comprising one or more, preferably two or more, or especially preferably all, of a GLP-1 receptor agonist, nicotinamide and an adenylate cyclase activator).

Stem cells which may be used in the method of directed differentiation (method of preparation) of the present invention may be cultured/maintained by conventional methods used in the art.

Cultivation of mammal-derived ES cells may be performed by conventional methods. For example, such ES cells may be maintained using mouse embryonic fibroblast (MEF) cells as feeder cells in a medium supplemented with leukemia inhibitory factor, KSR (KnockOut™ Serum Replacement), fetal bovine serum (FBS), non-essential amino acids, L-glutamine, pyruvic acid, penicillin, streptomycin and β-mercaptoethanol (e.g., DMEM medium).

Cultivation of iPS cells may also be performed by conventional methods. For example, iPS cells may be maintained using MEF cells as feeder cells in a medium supplemented with bFGF, KSR (KnockOut™ Serum Replacement), non-essential amino acids, L-glutamine, penicillin, streptomycin and β-mercaptoethanol (e.g., DMEM/F12 medium).

Using these stem cells as a raw material, it is possible to prepare insulin-producing cells by the method of directed differentiation of the present invention. Further, it is possible to obtain insulin-producing cells without xenoantigen contamination by using the method of directed differentiation of the present invention in a xeno-free culture system.

1-1. Step (1) of the present invention consists of two steps of step (1-1) and step (1-2), and is characterized by (1-1) culturing stem cells in a medium comprising an activator of activin receptor-like kinase-4/-7 and a GSK3 inhibitor and then (1-2) culturing in a medium comprising an activator of activin receptor-like kinase-4/-7.

Preferably, the medium in (1-2) in step (1) of the present invention does not substantially comprise a GSK3 inhibitor.

With this step, it is possible to direct stem cells to differentiate into endodermal cells.

The activator of activin receptor-like kinase (ALK)-4/-7 used in this step is selected from substances which have an activating effect on ALK-4 and/or ALK-7. Specific examples of the activator of activin receptor-like kinase-4/-7 used in this step include, but are not limited to, activin, Nodal and Myostatin. Among them, activin is preferable.

In this step, any activin may be used from the known activins of A, B, C, D and AB. As an activin used in this step, activin A is particularly preferable. Further, activins derived from any mammal (e.g., human or mouse) may be used. However, it is preferable to use an activin derived from the same animal species from which stem cells used for differentiation are derived. For example, when human-derived stem cells are the starting material, human-derived activin, especially human-derived activin A may be used preferably. These activins are commercially available.

The concentration of the activator of activin receptor-like kinase-4/-7 in the medium in this step may be selected appropriately depending on the type of the activator used. When human activin A is used, the concentration is usually 0.1-200 ng/ml, preferably 5-150 ng/ml, and especially preferably 10-100 ng/ml.

The type and concentration of the activator of activin receptor-like kinase-4/-7 used in step (1-1) and step (1-2) of step (1) may be the same or different from each other. However, the same activator and the same concentration are preferable.

This step is characterized by using a medium comprising a GSK3 inhibitor together with an activator of activin receptor-like kinase-4/-7.

The GSK3 inhibitor used in this step is selected from a group consisting of substances having GSK3α inhibitory activity, substances having GSKβ inhibitory activity and substances having both GSK3α inhibitory activity and GSKβ inhibitory activity. As the GSK3 inhibitor used in this step, a substance having GSKβ inhibitory activity or a substance having both GSK3α inhibitory activity and GSKβ inhibitory activity is preferable.

Specific examples of the above-mentioned GSK3 inhibitor include, but are not limited to, CHIR98014, CHIR99021, Kenpaullone, AR-AO144-18, TDZD-8, SB216763, BIO, TWS-119 and SB415286. These substances are commercially available. Even when commercially unavailable, one of ordinary skill in the art could prepare according to prior art literature.

It is also possible to use antisense oligonucleotide, siRNA or the like to the mRNA of GSK3 as a GSK3 inhibitor. Any of these substances is commercially available or can be synthesized according to prior art literature.

The GSK3 inhibitor used in this step is preferably selected from the group consisting of CHIR99021 (6-[[2-[[4-(2,4-dichlorophenyl)-5-(4-methyl-1H-imidazol-2-yl)-2-pyrimidinyl]amino]ethyl]amino]nicotinonitrile), SB216763 (3-(2,3-dichlorophenyl)-4-(1-methyl-1H-indole-3-yl)-1H-pyrrole-2,5-dione) and SB415286 (3-[(3-chloro-4-hydroxyphenyl)amino]-4-(2-nitrophenyl)-1H-pyrrole-2,5-dione). Particularly preferable is CHIR99021.

The concentration of GSK3 inhibitor in the medium is appropriately selected depending on the type of GSK3 inhibitor used. When CHIR99021 is used as a GSK3 inhibitor, the concentration thereof is usually 0.1-20 μM and preferably 1-5 μM. When SB415286 is used as a GSK3 inhibitor, the concentration thereof is usually 0.1-20 μM and preferably 1-10 μM. When SB216763 is used as a GSK3 inhibitor, the concentration thereof is usually 0.1-30 μM and preferably 0.5-20 μM.

This step is characterized by using a medium comprising a GSK3 inhibitor together with an activator of activin receptor-like kinase-4/-7 and a medium comprising an activator of activin receptor-like kinase-4/-7. Preferably, the latter medium comprising an activator of activin receptor-like kinase-4/-7 is a medium which does not substantially comprise a GSK3 inhibitor. By culturing stem cells under such conditions, it is possible to differentiate the cells into endodermal cells more favorably.

The "medium which does not substantially comprise a GSK3 inhibitor" mentioned above means not adding any GSK3 inhibitor positively to the medium, and does not mean to exclude that a trace amount of GSK3 inhibitor is contained in a medium for culturing stem cells. For example, it is possible to culture stem cells in a medium that comprises an activator of activin receptor-like kinase-4/-7 but "does not substantially comprise a GSK3 inhibitor" by culturing stem cells in a medium comprising a GSK3 inhibitor together with an activator of activin receptor-like kinase-4/-7 and then exchanging the medium with a medium to which an activator of activin receptor-like kinase-4/-7 has been added but a GSK3 inhibitor has not been added.

The medium used in this step is not particularly limited. A medium may be used which is prepared by adding an activator of activin receptor-like kinase-4/-7 or activator of activin receptor-like kinase-4/-7 together with a GSK3 inhibitor to a medium (hereinafter, sometimes referred to as "basal medium") conventionally used for culturing stem cells.

Specific examples of the above-mentioned basal medium include, but are not limited to, BME medium, BGjB medium, CMRL1066 medium, Glasgow MEM medium, Improved MEM medium, IMDM medium, Medium 199, Eagle's MEM medium, αMEM medium, DMEM medium, Ham's medium, RPMI 1640 medium, Fischer's medium and mixed media thereof. Any of them may be used as long as it is capable for culturing animal cells. These media are commercially available.

The medium used in the present invention may be either a serum-containing medium or a serum-free medium. The term "serum-free medium" means a medium not comprising an unadjusted or unpurified serum. It should be noted that those media in which purified blood-derived components or animal tissue-derived components (such as growth factors) have been mixed fall within serum-free media. When the medium used in this step is a serum-containing medium, a mammal serum such as fetal bovine serum may be used. Preferably, the medium used in this step is a serum-free medium. More preferably, the medium is a serum-free medium not comprising chemically undefined components.

The medium used in this step may comprise a serum replacement. Specific examples of serum replacements include, but are not limited to, albumin, transferrin, fatty acids, procollagens, trace elements (e.g., zinc or selenium), B-27 supplement, N2 supplement, KnockOut™ Serum Replacement (KSR), 2-mercaptoethanol, 3'-thiolglycerol and equivalents thereof. These serum replacements are commercially available. Preferably, xeno-free B-27 supplement or xeno-free KnockOut™ Serum Replacement (KSR) may be enumerated. For example, such a serum replacement may be added to a medium at a concentration of 0.01-10% by weight, preferably 0.1-2.0% by weight.

The medium used in this step may further comprise other additives, such as lipids, amino acids (e.g., non-essential amino acids), vitamins, growth factors, cytokines, antioxidants, 2-mercaptoethanol, pyruvic acid, buffering agents, inorganic salts, antibiotics (e.g., penicillin or streptomycin) or antimicrobial agents (e.g., amphotericin B) and the like.

The medium used in this step is especially preferably a serum-free medium comprising chemically defined raw materials alone. With the use of such a medium, it is possible to obtain differentiated cells with less or no xenoantigen contamination.

In this step, B-27 supplement-added DMEM medium is used preferably.

This step is carried out by culturing stem cells at temperatures appropriate for culturing the stem cells used (usually 30-40° C., preferably around 37° C.) in a $CO_2$ incubator. The period of culture is 2-10 days (preferably 2-6 days) for the entire step; and 1-3 days (preferably 1-2 days) for step (1-1) and 1-7 days (preferably 2-5 days) for step (1-2).

In this step, confirmation of differentiation of stem cells into endodermal cells may be performed by evaluating changes in the expression of endodermal cell-specifically expressed proteins and genes (hereinafter, sometimes referred to as "endoderm markers"). The evaluation of changes in the expression of the above-mentioned endoderm markers may be performed, for example, by a method of evaluating protein expression using antigen-antibody reaction, a method of evaluating gene expression using quantitative RT-PCR, or the like. Specific examples of the endoderm markers include, but are not limited to, SOX17 and FOXA2.

1-2. Step (2) is characterized by culturing the cells obtained in step (1) above in a medium comprising a hedgehog signaling inhibitor and an FGF. Through this step, it is possible to direct endodermal cells to differentiate into primitive gut tube cells.

The hedgehog signaling inhibitor used in this step is not particularly limited as long as it is a substance having a hedgehog signaling inhibitory activity. The substance may be either a substance occurring in nature or a chemically synthesized substance. Preferable examples of hedgehog signaling inhibitor include, but are not limited to, cyclopamine, KAAD-cyclopamine (28-[2-[[6-[(3-phenylpropanoyl)amino]hexanoyl]amino]ethyl]-17β, 23β-epoxy veratraman-3-one), KAAD-cyclopamine analogs, jervine (17, 23β-epoxy-3β-hydroxyveratraman-11-on), jervine analogs, SANT-1 and hedgehog pathway blocking antibodies. Among them, KAAD-cyclopamine is particularly preferable.

The concentration of the hedgehog signaling inhibitor in the medium in this step is appropriately selected depending on the type of the inhibitor used. The concentration is preferably 0.01-5 μM, more preferably 0.02-2 μM, and still further preferably 0.1-0.5 μM.

The medium in this step is a medium further comprising an FGF. It is possible to enhance the efficiency of directed differentiation by adding an FGF together with a hedgehog signaling inhibitor to the medium.

Specific examples of FGF which may be used in this step include, but are not limited to, FGF-1, FGF-2 (bFGF), FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22 and FGF-23. Among them, FGF-2 (bFGF), FGF-5, FGF-7 and FGF-10 are preferable. Still more preferable is FGF-10. These may be may be either natural type proteins or recombinant proteins.

The concentration of the FGF in the medium in this step is preferably 5-150 ng/ml, more preferably 10-100 ng/ml, and still more preferably 20-80 ng/ml.

In this step, an especially preferable combination is KAAD-cyclopamine and FGF-10.

The medium used in this step is prepared by adding a hedgehog signaling inhibitor and an FGF to the basal medium as illustrated in step (1) (the basal medium may comprise, if desired, various additives, sera or serum replacements as illustrated in step (1)). The medium used in this step may be prepared by using the same type basal medium as used in step (1). Alternatively, the medium used in this step may be prepared by using a different type basal medium from the one used in step (1). Preferably, B-27 supplement-added RPMI 1640 medium is used. It should be noted that in this step, a lower concentration B-27 supplement is preferably used, relative to the concentration in step (1).

This step is carried out by culturing resultant cells at temperatures appropriate for culturing the stem cells used (usually 30-40° C., preferably around 37° C.) in a $CO_2$ incubator. The period of culture is 1-5 days (preferably 1-3 days, more preferably 1-2 days).

In this step, confirmation of differentiation of endodermal cells into primitive gut tube cells may be performed by evaluating changes in the expression of primitive gut tube cell-specifically expressed proteins and genes (hereinafter, sometimes referred to as "primitive gut tube cell markers"). The evaluation of changes may be performed, for example, by a method of evaluating protein expression using antigen-antibody reaction, a method of evaluating gene expression using quantitative RT-PCR, or the like. Specific examples of the above-mentioned cell markers include, but are not limited to, FOXA2, HNF1b and HNF4a.

1-3. Step (3) is characterized by culturing the cells obtained in step (2) above in a medium comprising a retinoic acid receptor agonist, a hedgehog signaling inhibitor and a BMP signaling inhibitor. Preferably, step (3) is characterized by culturing the cells in a medium further comprising a TGF-β type I activin receptor-like kinase-4/-5/-7 inhibitor. Through this step, it is possible to direct primitive gut tube cells to differentiate into pancreatic progenitor cells.

The retinoic acid receptor (RAR) agonist used in this step may be either a naturally occurring retinoid, a chemically synthesized retinoid, a retinoic acid receptor agonist compound without retinoid backbone or a naturally occurring substance having retinoic acid receptor agonist activity. As an example of naturally occurring retinoid with RAR agonist activity, retinoic acids (isomers thereof are also included) may be given. Examples of retinoic acids include, but are not limited to, all-trans isomer (tretinoin) and 9-cis-retinoic acid (9-cis RA). Chemically synthesized retinoids are known in the art. Examples of retinoic acid receptor agonist compounds without retinoid backbone include, but are not limited to, Am80, AM580, TTNBP and AC55649. Examples of naturally occurring substances having retinoic acid receptor agonist activity include, but are not limited to, honokiol and magnolol. The RAR agonist used in this step is preferably retinoic acid, AM580 (4-[[5,6,7,8-tetrahydro-5,5,8,8-tetramethyl-2-naphthalenyl]carboxamide]benzoic acid), TTNPB (4-[[E]-2-[5,6,7,8-tetrahydro-5,5,8,8-tetramethyl-2-naphthalenyl]-1-propenyl]benzoic acid) and AC55649 (4'-octyl-[1,1'-biphenyl]-4-carboxylic acid). More preferably, retinoic acid is used. The concentration in the medium of the RAR agonist used in this step is appropriately selected depending on the type of RAR agonist used. When retinoic acid is used as a RAR agonist, the concentration is usually 0.1-100 μM, preferably 0.5-10 μM. When TTNPB is used as a RAR agonist, the concentration is usually 0.02-20 μM, preferably 0.05-10 μM. When AM580 is used as a RAR agonist, the concentration is usually 0.02-20 μM, preferably 0.05-10 μM. When AC55649 is used as a RAR agonist, the concentration is usually 0.02-20 μM, preferably 0.1-10 μM.

As examples of the hedgehog signaling inhibitor used in this step, those inhibitors enumerated in step (2) above may be given. Especially preferable is KAAD-cyclopamine. The hedgehog signaling inhibitor used in this step may be the same as used in step (2), or may be different from the one used in step (2). The concentration in the medium of the hedgehog signaling inhibitor used in this step is appropriately selected depending on the type of the inhibitor used. The concentration is preferably 0.01-5 μM, more preferably 0.02-2 μM, and still more preferably 0.1-0.5 μM.

The BMP signaling inhibitor used in this step means a compound that has inhibitory activity against the BMP signal transduction conducted via the binding of BMP and BMP receptor (type I or II). The BMP signaling inhibitor encompasses proteinaceous inhibitors and low molecular weight inhibitors. Examples of the proteinaceous inhibitor include, but are not limited to, natural inhibitors NOGGIN, CHORDIN, FOLLISTATIN, CERBERUS and GREMLIN. It is known that NOGGIN inhibits BMP signal transduction by inhibiting the binding of BMP4 to BMP receptor. As examples of the low molecular weight inhibitor, compounds which inhibit BMP2, BMP4, BMP6 or BMP7 that has an ability to activate a transcription factor SMAD1, SMAD5 or SMAD8 may be given. For example, DORSOMORPHIN (6-[4-(2-piperidin-1-ylethoxy)phenyl]-3-pyridin-4-ylpyrazolo[1,5-a]pyrimidine) and derivatives thereof may be enumerated. In addition to the above compounds, LDN-193189 (4-(6-(4-piperazin-1-yl) phenyl)pyrazolo[1,5-a] pyridin-3-yl)quinoline) and derivatives thereof may be enumerated as BMPI receptor kinase inhibitors. These compounds are commercially available. When they are unavailable, they may be prepared according to prior art literature. Among the compounds enumerated above, NOGGIN is especially preferable as a BMP signaling inhibitor used in this step.

The concentration of BMP signaling inhibitor in the medium is selected appropriately depending on the type of the inhibitor used. When NOGGIN is used, the concentration is usually 10 ng/ml-1000 ng/ml, preferably 50 ng/ml-500 ng/ml, more preferably 100 ng/ml-500 ng/ml, and most preferably 200 ng/ml-300 ng/ml.

The TGF-β type I activin receptor-like kinase-4/-5/-7 inhibitor used in this step optionally is selected from those compounds that have inhibitory activity against at least one TGF-β type I activin receptor-like kinase (ALK) selected from the group consisting of ALK-4, ALK-5 and ALK-7. Examples of ALK-4/-5/-7 inhibitors used in this step include, but are not limited to, SB-431542, SB-505124, SB-525334, A-83-01, GW6604, LY580276, ALK5 inhibitor II, TGF-β RI kinase inhibitor VIII and SD-208. These compounds are commercially available. When they are unavailable, they may be prepared according to prior art literature.

It is also possible to use an antisense oligonucleotide or siRNA to the mRNA of ALK-4, -5 or -7 as an ALK-4/-5/-7 inhibitor.

As ALK-4/-5/-7 inhibitor used in this step, SB-431542 (4-[4-(1,3-benzodioxol-5-yl)-5-(2-pyridinyl)-1H-imidazol-2-yl]-benzamide or hydrates thereof), A-83-01 (3-[6-methyl-2-pyridinyl]-N-phenyl-4-[4-quinolinyl]-1H-pyrazol-1-carbothioamide), ALK5 inhibitor II (2-[3-[6-methylpyridin-2-yl]-1H-pyrazol-4-yl]-1,5-naphthyridine) and TGF-β RI kinase inhibitor VIII (6-[2-tert-butyl-5-[6-methyl-pyridin-2-yl]-1H-imidazol-4-yl]-quinoxaline) are preferable; and SB-431542 (4-[4-(1,3-benzodioxol-5-yl)-5-(2-pyridinyl)-1H-imidazol-2-yl]-benzamide or hydrates thereof) is more preferable.

The concentration of ALK-4/-5/-7 inhibitor in the medium is selected appropriately depending on the type of the inhibitor used. When SB-431542 is used as ALK-4/-5/-7 inhibitor, the concentration is usually 0.1-50 μM and preferably 1-20 μM. When ALK5 inhibitor II is used, the concentration is usually 0.05-50 μM and preferably 0.2-10

μM. When A-83-01 is used, the concentration is usually 0.05-50 μM and preferably 0.1-10 μM. When TGF-β RI kinase inhibitor VIII is used, the concentration is usually 0.05-50 μM and preferably 0.1-10 μM.

The medium used in this step is prepared by adding to the basal medium illustrated in step (1) above (which may optionally comprise various additives, sera or serum replacements illustrated in step (1) above) a retinoic acid receptor agonist, a hedgehog signaling inhibitor and a BMP signaling inhibitor (preferably, further adding thereto a TGF-β type I activin receptor-like kinase-4/-5/-7 inhibitor). The medium used in this step may be prepared by using the same type basal medium as used in step (1) or (2) above. Alternatively, the medium used in this step may be prepared by using a different type basal medium from the one used in step (1) or (2) above. Preferably, B-27 supplement-added DMEM medium is used.

This step is carried out by culturing resultant cells at temperatures appropriate for culturing the stem cells used (usually 30-40° C., preferably around 37° C.) in a $CO_2$ incubator. The period of culture is 2-10 days (preferably 3-9 days, more preferably 5-8 days).

In this step, confirmation of differentiation of primitive gut tube cells into pancreatic progenitor cells may be performed by evaluating changes in the expression of pancreatic progenitor cell-specifically expressed proteins and genes (hereinafter, sometimes referred to as "pancreatic progenitor cell markers"). The evaluation of changes may be performed, for example, by a method of evaluating protein expression using antigen-antibody reaction, a method of evaluating gene expression using quantitative RT-PCR, or the like. Specific examples of the above-mentioned cell markers include, but are not limited to, PDX1, HNF6 and SOX9.

1-4. Step (4) is characterized by culturing the cells obtained in step (3) above in a medium comprising a TGF-β type I activin receptor-like kinase-4/-5/-7 inhibitor and a BMP signaling inhibitor. Preferably, this step is characterized by culturing the cells in a medium further comprising a protein kinase C activator. Through this step, it is possible to direct pancreatic progenitor cells to differentiate into endocrine progenitor cells.

The TGF-β type I activin receptor-like kinase-4/-5/-7 inhibitor used in this step is selected from those compounds that have inhibitory activity against at least one TGF-β type I activin receptor-like kinase (ALK) selected from the group consisting of ALK-4, ALK-5 and ALK-7. Examples of ALK-4/-5/-7 inhibitors used in this step include, but are not limited to, SB-431542, SB-505124, SB-525334, A-83-01, GW6604, LY580276, ALK5 inhibitor II, TGF-β RI kinase inhibitor VIII and SD-208. These compounds are commercially available. When they are unavailable, they may be prepared according to prior art literature.

It is also possible to use an antisense oligonucleotide or siRNA to the mRNA of ALK-4, -5 or -7 as an ALK-4/-5/-7 inhibitor.

As ALK-4/-5/-7 inhibitor used in this step, SB-431542 (4-[4-(1,3-benzodioxol-5-yl)-5-(2-pyridinyl)-1H-imidazol-2-yl]-benzamide or hydrates thereof), A-83-01 (3-[6-methyl-2-pyridinyl]-N-phenyl-4-[4-quinolinyl]-1H-pyrazol-1-carbothioamide), ALK5 inhibitor II (2-[3-[6-methylpyridin-2-yl]-1H-pyrazol-4-yl]-1,5-naphthyridine) and TGF-β RI kinase inhibitor VIII (6-[2-tert-butyl-5-[6-methyl-pyridin-2-yl]-1H-imidazol-4-yl]-quinoxaline) are preferable; and ALK5 inhibitor II is more preferable.

The concentration of ALK-4/-5/-7 inhibitor in the medium is selected appropriately depending on the type of the inhibitor used. When ALK5 inhibitor II is used as ALK-4/-5/-7 inhibitor, the concentration is usually 0.05-50 μM and preferably 0.2-10 μM. When SB-431542 is used, the concentration is usually 0.1-50 μM and preferably 1-20 μM. When A-83-01 is used, the concentration is usually 0.05-50 μM and preferably 0.1-10 μM. When TGF-β RI kinase inhibitor VIII is used, the concentration is usually 0.05-50 μM and preferably 0.1-10 μM.

As examples of the BMP signaling inhibitor used in this step, BMP signaling inhibitors illustrated in step (3) above may be given. Especially preferable is NOGGIN. The BMP signaling inhibitor used in this step may be either the same as the one used in step (3) or different from the one used in step (3). The concentration in the medium of the BMP signaling inhibitor used in this step may be selected appropriately depending on the type of the inhibitor. When NOGGIN is used, the concentration is usually 10 ng/ml-1000 ng/ml, preferably 50 ng/ml-500 ng/ml, more preferably 100 ng/ml-500 ng/ml, and most preferably 200 ng/ml-300 ng/ml.

The protein kinase C activator optionally used in this step is not particularly limited. As long as a substance has an activity to activate protein kinase C signal transduction and to direct endodermal lineage cells toward pancreatic specialization, the substance may be used. Specific examples of protein kinase C activator include, but are not limited to, (−)-indolactam V (ILV), (2S,5S)-(E,E)-8-(5-(4-(trifluoromethyl)phenyl)-2,4-pentadienoylamino) benzolactam, phorbol-12-myristate-13-acetate and phorbol-12,13-dibutyrate. Preferably, ILV is used. The concentration in the medium of the protein kinase C activator used in this step is appropriately selected depending on the type of the activator used. When ILV is used, the concentration is usually 1-1000 nM, preferably 10-500 nM.

The medium used in this step is prepared by adding to the basal medium illustrated in step (1) above (which may optionally comprise various additives, sera or serum replacements illustrated in step (1) above) a TGF-β type I activin receptor-like kinase-4/-5/-7 inhibitor and a BMP signaling inhibitor (preferably, further adding thereto a protein kinase C activator). The medium used in this step may be prepared by using the same type basal medium as used in step (1), (2) or (3) above. Alternatively, the medium used in this step may be prepared by using a different type basal medium from the one used in step (1), (2) or (3) above. Preferably, B-27 supplement-added DMEM medium is used.

This step is carried out by culturing resultant cells at temperatures appropriate for culturing the stem cells used (usually 30-40° C., preferably around 37° C.) in a $CO_2$ incubator. The period of culture is 1-5 days (preferably 1-3 days, more preferably 2-3 days).

In this step, confirmation of differentiation of pancreatic progenitor cells into endocrine progenitor cells may be performed by evaluating changes in the expression of endocrine progenitor cell-specifically expressed proteins and genes (hereinafter, sometimes referred to as "endocrine progenitor cell markers"). The evaluation of changes may be performed, for example, by a method of evaluating protein expression using antigen-antibody reaction, a method of evaluating gene expression using quantitative RT-PCR, or the like. Specific examples of the above-mentioned cell markers include, but are not limited to, NGN3, PAX4 and NEUROD1.

1-5. Step (5) is characterized by culturing the cells obtained in step (4) above in a medium comprising a phosphodiesterase inhibitor. Preferably, this step is characterized by culturing the cells in a medium further comprising one or more members, preferably two or more members, or especially preferably all members of the group consisting of a GLP-1 receptor agonist, nicotinamide and an adenylate cyclase activator. Through this step, it is possible to direct endocrine progenitor cells to differentiate into pancreatic endocrine cells.

The phosphodiesterase inhibitor used in this step is a compound that increases the intracellular concentration of cAMP or cGMP by inhibiting phosphodiesterase (PDE). As long as a compound has such an activity, the compound may be used without particular limitation. Specific examples of phosphodiesterase inhibitor include, but are not limited to, IBMX (3-isobutyl-1-methylxanthin) and dibutyl cAMP. Preferably, IBMX is used. The concentration of phosphodiesterase inhibitor is selected appropriately depending on the type of the inhibitor used. When IBMX is used, the concentration is usually 5-1000 µM, preferably 50-500 µM. When dibutyl cAMP issued, the concentration is usually 10-4000 µM, preferably 100-1000 µM.

The GLP-1 receptor agonist optionally used in this step is a substance having an activity as an agonist to the receptor of GLP-1 (glucagon-like peptide-1). Specific examples of GLP-1 receptor agonist include, but are not limited to, GLP-1, GLP-1MR agent, NN-2211, AC-2993 (exendin-4), BIM-51077, Aib(8,35) hGLP-1 (7,37) $NH_2$ and CJC-1131. Among them, exendin-4 is especially preferable. These substances are commercially available. When unavailable, they may be prepared according to prior art literature. In addition to the above-listed substances, a number of GLP-1 receptor agonists are available in the market and they may also be used in this step. The concentration of GLP-1 receptor agonist in the medium is selected appropriately depending on the type of the agonist used. When exendin-4 is used, the concentration is usually 1-1000 ng/ml, preferably 10-500 ng/ml, and more preferably 20-200 ng/ml.

In this step, nicotinamide (also called niacin or nicotinic acid amide) may be added to the medium. It has been reported that nicotinamide inhibits the death of pancreatic β-cells with its function as a poly(ADP-ribose) synthesis inhibitor. The concentration of the nicotinamide in the medium is usually 0.1-20 mM, preferably 5-20 mM.

In this step, an adenylate cyclase activator may be added to the medium. Specific examples of adenylate cyclase activator include, but are not limited to, forskolin and derivatives thereof. The concentration of adenylate cyclase activator in the medium is selected appropriately depending on the type of the activator used. When forskolin is used, the concentration is usually 0.1-100 µM, preferably 2-50 µM.

The medium used in this step is prepared by adding to the basal medium illustrated in step (1) above (which may optionally comprise various additives, sera or serum replacements illustrated in step (1) above) a phosphodiesterase inhibitor. It is preferred that one or more members, preferably two or more members, or especially preferably all members of the group consisting of a GLP-1 receptor agonist, nicotinamide and an adenylate cyclase activator are further added to the medium. The medium used in this step may be prepared by using the same type basal medium as used in any one of steps (1) to (4) above. Alternatively, the medium used in this step may be prepared by using a different type basal medium from the one(s) used in steps (1) to (4) above. Preferably, B-27 supplement-added DMEM/F12 medium is used.

This step is carried out by culturing resultant cells at temperatures appropriate for culturing the stem cells used (usually 30-40° C., preferably around 37° C.) in a $CO_2$ incubator. The period of culture is 1-15 days (preferably 2-10 days, more preferably 5-10 days).

In this step, confirmation of differentiation of endocrine progenitor cells into pancreatic endocrine cells may be performed by evaluating changes in the expression of pancreatic endocrine cell-specifically expressed proteins and genes (hereinafter, sometimes referred to as "pancreatic endocrine cell markers"). The evaluation of changes may be performed, for example, by a method of evaluating protein expression using antigen-antibody reaction, a method of evaluating gene expression using quantitative RT-PCR, or the like. It is also possible to evaluate such changes by determining the amounts of pancreatic hormones secreted into the medium. The determination of the amounts of pancreatic hormones secreted into the medium may be performed by western blotting analysis, ELISA or methods based on such methods. Specific examples of the above-mentioned cell markers include, but are not limited to, INS, GCG and SST.

As described so far, the present invention provides a method for directed differentiation of stem cells into insulin-producing cells. When steps (2) to (5) of the present invention are used, it is also possible to efficiently differentiate endodermal cells (other than those endodermal cells obtained through step (1) of the present invention) as a starting material into pancreatic progenitor cells. Therefore, the present invention also relates to a method for directed differentiation of endodermal cells as a starting material into insulin-producing cells. Briefly, the present invention provides a method for directed differentiation into insulin-producing cells, comprising culturing stem cell-derived endodermal cells in the following steps (a) to (d):

(a) a step of culturing the endodermal cells in a medium comprising a hedgehog signaling inhibitor and an FGF;
(b) a step of culturing the cells obtained in step (a) in a medium comprising a retinoic acid receptor agonist, a hedgehog signaling inhibitor and a BMP signaling inhibitor (preferably, further comprising a TGF-β type I activin receptor-like kinase-4/-5/-7 inhibitor);
(c) a step of culturing the cells obtained in step (b) in a medium comprising a TGF-β type I activin receptor-like kinase-4/-5/-7 inhibitor and a BMP signaling inhibitor (preferably, further comprising a protein kinase C activator); and
(d) a step of culturing the cells obtained in step (c) in a medium comprising a phosphodiesterase inhibitor (preferably, further comprising one or more members, preferably two or more members, or especially preferably all members of the group consisting of a GLP-1 receptor agonist, nicotinamide and an adenylate cyclase activator).

Examples of the substances added to the individual steps are the same as described above.

With the method of directed differentiation of the present invention, it is possible to efficiently direct stem cells to differentiate into insulin-producing cells. As a result, it becomes possible to supply a large quantity of cells which specifically produce insulin (i.e., cells secreting C-peptide in response to insulin secretion promoter and hyperglycemia whose insulin expression capacity is significantly superior compared to other pancreatic hormones). These insulin-producing cells may be used in medicines (especially, medicines for cell-based therapy) and as a tool for developing therapeutics for diabetes.

Hereinbelow, preferred embodiments of the present invention will be described with reference to several examples.

A characteristic in one preferred embodiment of the present invention resides in that while high concentration NOGGIN specifically enhances differentiation of undifferentiated stem cells into PDX1-positive pancreatic progenitor cells and then into NGN3-expressing pancreatic endocrine progenitor cells, the NOGGIN plays an important role in inhibiting induction into hepatic or intestinal cells. Further, a characteristic in another preferred embodiment of the present invention resides in that IBMX plays an important role together with exendin-4 and nicotinamide for differentiation into INSULIN-single positive cells expressing various markers of functionally matured β-cells. The cells resulting from directed differentiation using these preferred embodiments comprise endogenous C-peptide pools released in response to various insulin secretion promoters and high glucose.

A characteristic in still another preferred embodiment of the present invention resides in that according to the 5-step directed differentiation protocol described in the present specification, it is possible to prepare from hiPS cells functional INS-producing β-cells that possess endogenous insulin pools and can secrete insulin in a glucose-sensitive manner. Thus, it is possible to direct differentiation into mature INS single-positive pancreatic β-cells.

In one preferred embodiment of the method of the present invention, a combined treatment with RA, KAAD-cyclopamine, SB431542 and NOGGIN is used to induce pancreatic progenitor cells at stage 3. Hedgehog signaling has been reported to antagonize RA-mediated specification in pancreatic endocrine cells during zebrafish and mouse embryonic development. Therefore, use of KAAD-cyclopamine and RA at this stage is in agreement with their importance already known. In the differentiation system of the present invention, the number of AFP-positive cells decreased at high NOGGIN concentrations (200-300 ng/ml), which is consistent with previous reports that BMP is required for pancreatic differentiation but is inhibitory for hepatic differentiation. BMP signal transduction has also been reported to increase CDX2 expression through SMAD4, which might explain the downregulation of CDX2 by NOGGIN.

In another preferred embodiment of the method of the present invention, a combination of Alk5i, ILV and NOGGIN is applied at stage 4 to achieve efficient induction of EP cells from pancreatic progenitor cells. Thus, it is possible to induce a high proportion of NGN3-expressing EP cells most of which are co-expressing NEUROD1 and PAX4.

The NGN3 transcript was highly expressed at this stage and gradually disappeared within one or two or more days, which is consistent with the transient expression of this gene in vivo. NKX6.1, an important regulator of the differentiation of pancreatic endocrine cells (in particular, β-cells) was expressed in both stage-3 and stage-4 cells, indicating that the progenitor cells induced in the culture system of the present invention possess the potential to differentiate into pancreatic β-cells.

In another preferred embodiment of the method of the present invention, both IBMX and FRKL in addition to exendin-4 and nicotinamide are used at stage 5 to promote induction of C-peptide producing cells. IBMX and FRKL are known to increase the intracellular cAMP level, suggesting that the intracellular cAMP level is one of the key factors that enhance the differentiation of INS-positive cells.

Under every environment where IBMX and FRKL were used in combination, dominant C-peptide/PDX1 double-positive cells were observed. Although PDX1-positive cells not expressing C-peptide were also present, these cells were highly PDX1-positive and may be epithelial progenitor cells or precursors thereof. In addition to exendin-4 and nicotinamide, IBMX and FRKL similarly promote differentiation into C-peptide-positive cells. However, it is believed that the combination of exendin-4, nicotinamide and IBMX provides a better environment for the induction of endocrine progenitor cells to differentiate into INS-expressing cells. This assumption is based on the following observations. First, the numbers of SST-positive and CP/SST-double positive cells were relatively higher in FRKL-based environment than in IBMX-based environment, which suggested that although both IBMX and FRKL increased the intracellular cAMP level, FRKL might have promoted SST-positive cells by acting on other pathways. Second, the number of PDX1 single positive cells was also higher in FRKL-based environment than in IBMX-based environment, which reflects that FRKL acted for generating other cell types. Third, the expression levels of β-cell specific genes were relatively higher in IBMX-induced cells than in FRKL-induced cells.

The existence of polyhormonal cells has been reported during the primary transition stage of early fetal development in both rodents and humans. It is unknown whether polyhormonal cells represent pancreatic endocrine progenitor cells or immature cell types belonging to the fetal stage of pancreatic development. Previous studies reported that after transplantation, polyhormonal cells differentiated in vivo into GCG-expressing cells, and dynamic chromatin remodeling was reported to occur during this transition into matured cell types. Recently, it has been shown that human ES cell-derived pancreatic endoderm cells transplanted into immunodeficient mice underwent further differentiation and maturation into glucose-responsive INS-secreting cells, which suggests that the pancreatic precursors obtained in vitro could mature in vivo. The present inventors have demonstrated in the directed differentiation culture of the present invention that addition of IBMX effectively decreases polyhormonal cells and increases INS single-positive cells. Therefore, these results shows that it is possible to induce INS single-positive cells in vitro using the method of the present invention by activating proper signaling pathways at proper stages.

As a characteristic of the method of the present invention, both NOGGIN and IBMX play vital roles in the generation of INS single-positive cells from human iPS-derived cells. The present inventors have confirmed as one embodiment of the present invention that while addition of NOGGIN at stages 3 and 4 regardless of IBMX is essential for generation of INS-positive cells, it was confirmed that IBMX at stage 5 promotes and regulates the generation of INS single-positive cells in cooperation with high concentration NOGGIN (200 ng/ml) at stages 3 and 4. Therefore, the complexed effect of NOGGIN and IBMX from a combination of high concentration NOGGIN and IBMX as one embodiment of the present invention is important for improving endogenous C-peptide contents and glucose-stimulated C-peptide secretion and for generating functionally matured β-cells.

As a still another preferred embodiment of the present invention, there is provided a xeno-free directed differentiation system. Animal-derived substances are not desirable for clinical use. Therefore, in order to minimize the potential risk in clinical use in the future, human iPS cells must be generated, maintained and differentiated in a xeno-free culture system. According to the method described in the present specification, it is possible to differentiate stem cells (e.g., hiPS cells) into INS-positive cells using xeno-free scaffolds, supplements and factors for both maintenance and differentiation without using feeder cells.

2. Medicines Comprising the Cells

The present invention provides a medicine comprising insulin-producing cells generated by the above-described method of directed differentiation. The term "insulin-producing cells" used herein mean cells that secret C-peptide in response to insulin secretagogues or hyperglycemia and have a significantly superior capacity of insulin expression compared with expression capacities for other pancreatic hormones.

The method of directed differentiation of the present invention enables efficient generation of insulin-producing cells even in a xeno-free culture system. Therefore, the medicine of the present invention is free from xenoantigen contamination and safe when administered to mammals (e.g., human, mouse, rat, guinea pig, pig or monkey).

With respect to methods of administration (transplantation) of the medicine of the present invention to human patients, several methods may be enumerated. For example, a method in which a microincision is made in the right lower abdomen of a human patient, followed by exposure of a thin blood vessel of the mesentery into which a catheter is inserted in direct vision for cell transplantation; a method in which the hepatic portal vein is identified with echo and then a catheter is punctured thereinto to transplant cells; or a method in which cells are transplanted into the spleen by directly puncturing the spleen under the guide of abdominal echo (see Nagata H, Ito M, Shirota C, Edge A, McCowan T C, Fox I J: Route of hepatocyte delivery affects hepatocyte engraftment in the spleen. Transplantation, 76(4):732-4, 2003). Among them, the method of cell transplantation using echo is preferable since it is less invasive. As a specific example of this method, a method is given in which cells are transplanted into the spleen or the liver by direct puncture under the guide of abdominal echo. The amount of administration (transplantation) of the medicine of the present invention is, for example, $1 \times 10^8$-$1 \times 10^{10}$ cells/patient, preferably $5 \times 10^8$-$1 \times 10^{10}$ cells/patient, and more preferably $1 \times 10^9$-$1 \times 10^{10}$ cells/patient. It is preferred that insulin-producing cells prepared from patient's own cells or donor cells showing cytocompatibility or histocompatibility type tolerable for the patient are used. Especially preferable are such insulin-producing cells that were differentiated into (generated) in a xeno-free culture system. The amount of administration (transplantation) of medicine of the present invention may be appropriately varied depending on the age, body weight, symptoms, etc. of the patient.

Among the medicines of the present invention, those comprising insulin-producing cells enable insulin production (secretion) in the patient's body when they have been administered (transplanted) thereinto. Therefore, these medicines are useful in treating diabetes resulting from decrease in insulin production (secretion).

3. Method of Screening

The present invention also relates to a method of screening for therapeutics for diabetes using the insulin-producing cells prepared by the above-described method of directed differentiation of the present invention.

The method of screening of the present invention is carried out, for example, as described below. Briefly, insulin-producing cells obtained according to the method of directed differentiation of the present invention are cultured (a) in the presence of a test compound and (b) in the absence of the test compound. Then, intracellular insulin expression levels or extracellular insulin secretion levels in (a) and (b) are determined and compared.

As the insulin expression level, the expression level of insulin, the expression level of polynucleotide (e.g., mRNA) encoding insulin, or the like may be used. The expression level and secretion level of insulin may be determined by known methods; e.g., a method in which insulin in cell extract or medium may be measured using an antibody that recognizes insulin, by western blotting analysis, ELISA or a method based on such methods.

Expression levels of insulin mRNA may be determined by known methods; e.g., northern hybridization, S1 mapping, PCR, quantitative RT-PCR, DNA chip or array method, or methods based on these methods.

Cultivation of insulin-producing cells may be carried out according to any known method as long as under conditions where insulin is expressed and/or secreted. Specific examples of the culture medium used include, but are not limited to, MEM medium, DMEM medium, RPMI 1640 medium and 199 medium, all of which comprise approximately 1-20% fetal bovine serum.

The test compound is not particularly limited. For example, synthetic compounds, natural compounds, low molecular weight compounds, peptides, proteins, and animals/plants- or living body-derived extracts may be used.

With the screening method of the present invention, it is possible to detect either substances that inhibit insulin production or substances that promote insulin production. Substances that promote insulin production thus screened are useful as a therapeutic for diabetes.

EXAMPLES

Hereinbelow, the present invention will be described in more detail with reference to the following Examples. However, the present invention is not limited to these Examples.

(A) MATERIALS AND METHODS (1) Cell Line

A human iPS (hiPS) cell line was used. Toe, a hiPS cell line established by Toyoda et al. of the National Institute for Child Health and Development, Tokyo, Japan (Yamazoe et al., J Cell Sci 26, 5391-5399, 2013) was obtained from the cell bank of NIBIO (Japan). The cells were initially grown and maintained in an undifferentiated state under the xenogeneic conditions as described in Non-Patent Document No. 11.

(2) Cultivation of Undifferentiated hiPS Cells Under Xeno-Free Conditions

Freeze-stored hiPS cells were thawed and cultured on CellBIND cell culture dishes (Corning) coated with a xeno-free synthetic scaffold (Synthemax II-SC Substrate; Corning) under xeno-free conditions in hiPS cell maintenance medium. For xenogeneic culture, the maintenance medium was composed of Knockout DMEM/F12 (Life Technologies) supplemented with penicillin-streptomycin (50 units/ml penicillin, 50 μg/ml streptomycin; Nacalai Tesque), 2 mM L-glutamine (L-Gln; Nacalai Tesque), 1% nonessential amino acids (NEAA; Life Technologies), 0.1 mM 2-mercaptoethanol (2-ME; Sigma-Aldrich), 20% (v/v) knockout serum replacement (Kockout SR; Life Technologies), and 5 ng/ml recombinant human FGF2 (rhFGF2; Pepro Tech). On the other hand, for xeno-free culture, Knockout SR and rhFGF2 used in the xenogeneic maintenance medium were replaced with Knockout SR xeno-free Cell Therapy System (CTS; Life Technologies) and xeno-free rhFGF2 (Pepro Tech), respectively. The xeno-free maintenance medium was also supplemented with 1% Knockout SR growth factor cocktail CTS (Life Technologies). Undifferentiated hiPS cells were passaged at a ratio of 1:3 every 3-4 days by manually dissociating cell colonies with a cell dissociation buffer (Life Technologies) and collecting small clusters with a cell scraper (Asahi). Cells were initially grown under xenogeneic conditions and then sequentially passaged under xeno-free conditions before they were used for differentiation.

(3) In Vitro Differentiation of Undifferentiated hiPS Cells

For pancreatic differentiation, undifferentiated hiPS cells were dissociated with TrypLE Select CTS (Life Technologies) after three consecutive passages, collected with a cell scraper, and seeded at a density of $1 \times 10^5$ cells/well on 96-well CellBIND cell culture plates coated with Synthemax II-SC Substrate. The cells were cultured for 1 day in a xeno-free maintenance medium supplemented with 10 μM ROCK inhibitor (Y-27632; Wako), followed by another 1-2 days of culture without ROCK inhibitor to 80%-90% confluence. Then, the cells were directed toward the following key stages of pancreatic differentiation: definitive endoderm cells (DE; stage 1), primitive gut tube cells (PG; stage 2), pancreatic progenitor cells (PP; stage 3), endocrine progenitor cells (EP; stage 4) and hormone-expressing endocrine cells (EC; stage 5) (see FIG. 2).

At stage 1, first, cells were lightly washed with PBS not containing $Ca^{2+}$ and $Mg^{2+}$ (Sigma-Aldrich) for initiation of differentiation. Then, the cells were cultured for 2 days in DMEM-high glucose medium (Life Technologies) supplemented with penicillin-streptomycin, 2 mM L-Gln, 1% NEAA, 0.1 mM 2-ME, 2% (v/v) B27 supplement xeno-free CTS (Life Technologies), 100 ng/ml recombinant human activin A (Act; HumanZyme) and 3 μM CHIR99021 (TOCRIS Bioscience), and subsequently for another 3 days cultured without CHIR99021. The medium was replaced with fresh medium every one day.

At stage 2, cells were cultured in RPMI 1640 medium (Life Technologies) supplemented with penicillin-streptomycin, 2 mM L-Gln, 1% NEAA, 0.1 mM 2-ME, 1% (v/v) B27 supplement xeno-free CTS, 0.25 μM KAAD-cyclopamine (Cyc; Stemgent), and 50 ng/ml recombinant human fibroblast growth factor 10 (FGF10; PeproTech).

At stage 3, cells were cultured for 6 days in DMEM-high glucose medium supplemented with penicillin-streptomycin, 2 mM L-Gln, 1% NEAA, 0.1 mM 2-ME, 1% (v/v) B27 supplement xeno-free CTS, 2 μM all-trans retinoic acid (RA; Stemgent), 0.25 μM Cyc, 10 μM SB431542 (SB; TGF-β type I activin receptor-like kinase-4/-5/-7 inhibitor; CALBIOCHEM), and 200 ng/ml recombinant human NOGGIN (Nog; BMP signaling inhibitor; R&D Systems). The medium was changed every two days.

At stage 4, cells were cultured for 2 days in DMEM-high glucose medium supplemented with penicillin-streptomycin, 2 mM L-Gln, 1% NEAA, 0.1 mM 2-ME, 1% (v/v) B27 supplement xeno-free CTS, 5 μM Alk5i (TGF-β type I activin receptor-like kinase-4/-5/-7 inhibitor; CALBIOCHEM), 300 nM (−)indolactam V (ILV; R&D Systems) and 200 ng/ml Nog.

At stage 5, cells were cultured for 8 days in DMEM/F12 medium supplemented with penicillin-streptomycin, 2 mM L-Gln, 1% NEAA, 0.1 mM 2-ME and 1% (v/v) B27 supplement xeno-free CTS. To this medium were added 50 ng/ml exendin-4 (Ex-4; Cell Sciences), 10 mM nicotinamide (NA; Sigma-Aldrich), and/or 100 μM 3-isobutyl-1-methylxanthine (IBMX; phosphodiesterase inhibitor; Wako), and/or 10 μM forskolin (FRKL; adenylate cyclase activator; Wako). The media were changed every two days.

All components/factors of the medium were reconstituted using 0.1% human serum albumin (HAS; Sigma-Aldrich), PBS or DMSO for xeno-free culture. The same xeno-free culture technique was also used for maintenance and differentiation of hiPS cells on two other commercial xeno-free scaffolds, CELLstart (Life Technologies) and recombinant human vitronectin (rhVTN; Life Technologies).

(4) Flow Cytometry

Flow cytometry was performed for the xenoantigenic factor N-glycolylneuraminic acid (Neu5Gc) by the method of Martin et al. (Non-Patent Document No. 12) with some modifications. Briefly, cells were treated with a cell dissociation buffer at 37° C. for 15 min and recovered as a single cell suspension with a micropipette. After two washes with PBS, cells were washed once with 0.5% (v/v) blocking agent (BA, Sialix)-added PBS (0.5% BA/PBS). For staining, $1.0 \times 10^6$ cells in a total volume of 50 μl were incubated at 4° C. for 60 min with chicken anti-Neu5Gc IgY antibody (Ab) (1:200 dilution, Sialix), chicken IgY negative control (1:200 dilution, Sialix), or without a primary antibody, in 0.5% BA/PBS. After three washes with 0.5% BA/PBS, cells were incubated at 4° C. for 60 min with Alexa Fluor 488-conjugated donkey anti-chicken antibody (1:500, Molecular Probes) in 0.5% BA/PBS. Flow cytometry was performed on a BD FACSCanto Flow Cytometer (BD Biosciences) and analyzed using FlowJo software version 7.6.5 (Tree Star, Inc.).

(5) Quantitative RT-PCR Analysis

Total RNA was extracted from cells at each stage using TRI reagent (Sigma-Aldrich), followed by removal of genomic DNA contamination by digestion with deoxyribonuclease I (Sigma-Aldrich). Total RNA of human adult pancreas was purchased from Clontech. cDNA was prepared from 2.0 μg of RNA with oligo-dT primers and the ReverTraAce RT-reagent kit (TOYOBO). The primer sequences used for real-time PCR are summarized in Table 1 below together with the lengths thereof (The sequences of forward primers are designated as SEQ ID NOS: 1-30 from the top to downward; and the sequences of reverse primers as SEQ ID NOS: 31-60 from the top to downward.) Real-time PCT was carried out on a 7500 FAST Real-Time PCR System (Applied Biosystems). PCR amplification was carried out in a total 20 μl of reaction mixture comprising 10 μL of 2×Thunderbird SybrqPCR Mix (TOYOBO), 8.5 μL of Milli-Q water, 0.5 μL of 0.25 μM forward and reverse primers, and 1.0 μL of template cDNA. The reaction was terminated after 40 cycles (cycle conditions: 50° C. for 2 min, 95° C. for 10 min, 95° C. for 15 sec and 60° C. for 1 min). The expression of each target gene was normalized against the expression level of the housekeeping gene glyceraldehyde-3-phosphate dehydrogenase (GAPDH).

TABLE 1

| Genes | Primer sequences | | Product (bp) |
|-------|------------------|--|--------------|
|       | Forward          | Reverse | |
| GAPDH | CGAGATCCC TCCAAAATC AA | CATGAGTCC TTCCACGAT ACCAA | 288 |
| OCT3/4 | GTATTCAGC CAAACGACC ATC | CTGGTTCGC TTTCTCTTT CG | 176 |
| CER3 | GCCGATAGA TGGAATGAA AAT | AAAATGAAC AGACCCGCA TT | 244 |

TABLE 1-continued

| Genes | Forward | Reverse | Product (bp) |
|---|---|---|---|
| SOX17 | GCTTTCATGGTGTGGGCTAAG | CAGCGCCTTCCACGACTT | 108 |
| FOXA2 | CTGAGCGAGATCTACCAGTGGA | CAGTCGTTGAAGGAGAGCGAGT | 104 |
| HNF1β | ATAGCTCCAACCAGACTCACA | AGGCTGTGGATATTCGTCAA | 313 |
| HNF4α | CCAAGAGATCCATGGTGTTCAA | TTGATGTAGTCCTCCAAGCTCA | 274 |
| PDX1 | CTTGGAAACCAACAACTATTCAC | ATTAAGCATTTCCCACAAACA | 218 |
| HNF6 | AAATCACCATTTCCCAGCAG | AGCTTTTCCACCGAGGTTTT | 192 |
| NKX6.1 | CCAAGAAGAAGCAGGACTCG | TCAACAGCTGCGTGATTTTC | 126 |
| SOX9 | AAAGGCAACTCGTACCCAAATTT | AGTGGGTAATGCGCTTGGAT | 63 |
| PROX1 | AAAGCAAAGCTCATGTTTTTTATACC | GTAAACTCACGGAAATTGCTAAACC | 135 |
| HLXB9 | GCACCAGTTCAAGCTCAACA | GCCTTTTTGCTGCGTTTCCATTTC | 135 |
| CDX2 | CTCCTCCCCAGCTCTTCTCT | TCTTAGCTGCCTTTGGCTTC | 195 |
| AFP | TGCCAACTCAGTGAGGACAA | TCCAACAGGCCTGAGAAATC | 356 |
| NGN3 | TCGAGAGAGAGCGTGACAGA | CTACCGGCGCAAAAGAATAG | 175 |
| PAX4 | CAGACTGTGGCTCCTTCCTC | GGGTGCTCATAGGGAAAACA | 224 |
| NEUROD1 | CTCCTTCGTTCAGACGCTTT | GTGGAAGACATGGGAGCTGT | 226 |
| INS | CATCAGAAGAGGCCATCAAG | TCTTGGGTGTGTAGAAGAAGC | 200 |
| GCG | CAGAAGAGGTCGCCATTGTT | TGGCTAGCAGGTGATGTTGT | 192 |
| SST | CCAACCAGACGGAGAATGAT | AGGGAAGAGAGATGGGTGT | 241 |
| PPY | TGCCCATTTACTCTGGACTC | ATCTGCTCTGGTGTGGCATT | 160 |
| AMY | ATTCGCAAGTGGAATGGAGA | GCCCAACCCAATCATTAACA | 283 |
| ISL1 | ATTTCCCTATGTGTTGGTTGCG | CGTTCTTGCTGAAGCCGATG | 229 |
| MAF-A | TTCAGCAAGGAGGAGGTCAT | CGCCAGCTTCTCGTATTTCT | 216 |
| GCK | GGAGAGAAAGCGCTGAGGAC | CTGGTTTGGGGTTTGAGGTT | 160 |
| UCN3 | GAGGGAAGTCCACTCTCGGG | TGTTGAGGCAGCTGAAGATGG | 137 |
| IAPP | AGGCAGATCACAAGGTCAGG | GTGCAATCTCGGCTCACTG | 186 |
| SLC30A8 | TGTCCCAGAGAGAGACCAGA | CCACGACCTCTGCAATCATG | 163 |
| GLUT1 | GATTCCCAAGTGTGAGTCGC | GACATCATTGCTGGCTGGAG | 158 |

(6) Alkaline Phosphatase (AP) Staining

The cultured cells were fixed with 4% (w/v) paraformaldehyde (Nacalai Tesque), washed with PBS and then incubated with alkaline phosphatase buffer (100 mM Tris-HCl [pH 9.5], 100 mM NaCl, 50 mM $MgCl_2$ and 0.1% Tween-20) for 30 min at room temperature. The coloring reaction was carried out with 4-nitroblue tetrazolium chloride (35 μg/ml) and 5-bromo-4-chloro-3-indolyl phosphate (17.5 μg/ml) (Roche Diagnostics) in the dark for 30 min at room temperature. Cells were then washed with 1 mM EDTA/PBS and fixed with 4% paraformaldehyde. Finally, images were captured.

(7) Immunocytochemical Analysis

Cells were fixed with 4% paraformaldehyde, washed with PBS for 15 min and then permeabilized with 1% triton X-100 (Nacalai Tesque) for 10 min. After washing with PBST (0.1% tween-20 (Nacalai Tesque) in PBS), the cells were blocked with 20% (v/v) Blocking One (BO: Nacalai Tesque)-added PBST (20% BO/PBST) for 1 hr. Then, the cells were incubated with a primary antibody at 4° C. overnight. The following primary antibodies were used: mouse anti-OCT3/4 (1:100, Santa Cruz Biotechnology, sc-5279); rabbit anti-NANOG (1:100, ReproCELL, RCAB003P); mouse anti-SSEA4 (1:100, R&D Systems, BAM1435); mouse anti-TRA 1-81 (1:100, Millipore, MAB4381); rabbit anti-SOX2 (1:100, Millipore, AB5603); mouse anti-SSEA1 (1:100, BioLegend, 125603); goat anti-SOX17 (1:100, R&D Systems, AF1924); rabbit anti-HNF3β/FOXA2 (1:300, Millipore, #07-633); goat anti-HNF4a (1:100, Santa Cruz Biotechnology, SC-6556); goat anti-PDX1 (1:100, R&D Systems, AF2419); rabbit anti-HNF6 (1:100, Santa Cruz Biotechnology, sc-13050); rabbit anti-SOX9 (1:200, Millipore, AB5535); mouse anti-CDX2 (1:500, BioGenex, MU392-UC); mouse anti-AFP (1:200, MONOSAN, MON4035); sheep anti-NGN3 (1:200, R&D Systems, AF3444); rabbit anti-PAX4 (1:200, Abcam, ab42450); goat anti-NEUROPED1 (1:100, R&D Systems, AF2746); guinea pig anti-insulin (1:500, DAKO, A0564); rabbit anti-C-peptide (1:200, Cell Signaling Technology, #4593); mouse anti-glucagon (1:300, Sigma-Aldrich, G2654); goat anti-somatostatin (1:500, Santa Cruz Biotechnology, sc-7819); rabbit anti-somatostatin (1:500, DAKO, A0566); rabbit anti-pancreatic polypeptide (1:300, DAKO, A0619); mouse anti-amylase (1:100, Santa Cruz Biotechnology, sc-46657); rabbit anti-UCN3 (1:500, Phoenix Pharmaceuiticals, G-019-28); goat anti-ISL1 (1:100, R&D Systems, AF1837); and rabbit anti-IAPP (1:200, Abcam, ab15125). The next day, the cells were washed with PBST and then incubated with 1:1000 dilution of a secondary antibody (Alexa Fluor 488-, 568- or 633-conjugated donkey or goat anti-mouse, anti-goat, anti-rabbit, anti-sheep or anti-guinea pig IgG) (Molecular Probes) in the dark at room temperature for 2 hr. All the primary and secondary antibodies were diluted with 20% BO/PBST. Nuclei were counterstained with 4', 6-diamidino-2-phenylindole dihydrochloride (DAPI, Roche Applied Science). After three washes with PBST, images were captured using an ImageXpress Micro scanning system (Molecular Devices, Japan), followed by quantitative analysis using the MetaXpress cellular image analysis software (Molecular Devices, Japan).

(8) Analysis of C-Peptide Secretion and Secretion Level

The differentiated cells at the end of stage 5 were initially incubated at 37° C. for 30 min with DMEM (Life Technologies) containing minimal essential medium, 2.5 mM glucose and 1% B27 Supplement Xeno-Free CTS. This initial incubation was regarded as washing. Subsequently, the medium was discarded and then the cells were incubated with DMEM (100 µl per well) containing 2.5 mM glucose at 37° for 1 hr. After collecting the supernatant, the same cells were further cultured for 1 hr in 20 mM glucose-containing DMEM or 2.5 mM glucose-containing DMEM supplemented with various stimulants, e.g., 2 µM (−)-Bay K8644 (Sigma-Aldrich), 100 µM tolbutamide (Wako), 250 µM carbachol (Sigma-Aldrich), 0.5 mM IBMX or 30 mM potassium chloride (KCl) (Wako). The supernatant was collected again and stored at −20° C. until analysis. Finally, the cells were lysed with 0.01% Triton X-100 in PBS containing 1% protease inhibitor cocktail (Nacalai Tesque). Intracellular C-peptide and protein levels were quantitatively determined. C-peptide level was measured using a human C-peptide ELISA kit (ALPCO Diagnostics) according to the manufacturer's instructions. The total protein in cell lysate was quantitatively determined using a Bio-Rad reagent kit (Bio-Rad). The amount of C-peptide was normalized against the corresponding amount of the total protein.

(B) EXAMPLES AND COMPARATIVE EXAMPLES

Example 1: Self-Renewal and Maintenance of Undifferentiated hiPS Cells Under Xeno-Free Conditions Undifferentiated hiPS cells were cultured under xeno-free conditions in the same manner as described in subsection (2) in section (A) above. As a result, the present inventors have found that the levels of N-glycolylneuraminic acid (Neu5Gc), an indicator of xenogeneic contamination in human pluripotent stem cell cultures, markedly decreased to an undetectable level in hiPS cells grown under xeno-free conditions after passage 2 (P2). In addition, hiPS cells grown under xeno-free conditions (P3) retained their self-renewal capacity and pluripotency, as confirmed by alkaline phosphatase staining and the expression levels of OCT4, NANOG, SOX2, TRA1-81 and SSEA-4, which were similar to the corresponding expression levels in hiPS cells grown under xenogeneic conditions (P0). There was no detectable expression of SSEA-1, a marker associated with hiPS cell differentiation, suggesting that hiPS cells are maintained in an undifferentiated state under xeno-free conditions. As shown in FIG. 1, hiPS cells grown under xeno-free conditions up to about passage 30 exhibited a distinctive morphology of sharp-edged, flat, and tightly packed colony structures, which is a characteristic of pluripotent stem cells. Therefore, it was revealed that the xeno-free system of the present inventors is effective for keeping hiPS cells free of contamination from non-human derived factors, while maintaining their pluripotency.

Figure 2:
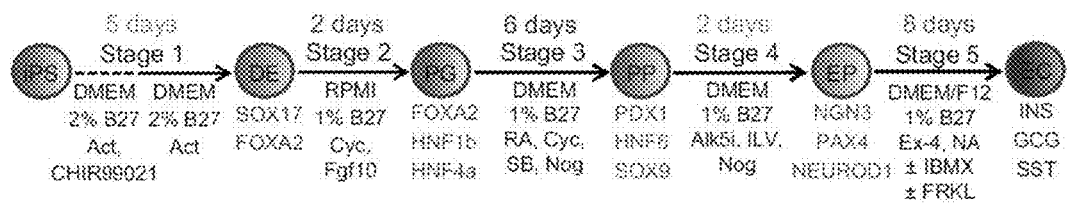
FIG. 2 An outline of one embodiment of the 5-step protocol of the present invention for differentiation in a xeno-free system is shown. Provided is a schematic drawing of the differentiation procedure into definitive endoderm cells (DE; stage 1), primitive gut tube cells (PG; stage 2), pancreatic progenitor cells (PP; stage 3), endocrine progenitor cells (EP; stage 4) and endocrine cells (EC; stage 5). Abbreviations used are as follows: Act (activin A), CHIR99021 (GSK3β-specific inhibitor), Fgf10 (fibroblast growth factor-10), Cyc (KAAD-cyclopamine), Nog (NOGGIN), RA (retinoic acid), SB (SB431542; TGF-β type I activin receptor-like kinase-4/-5/-7 inhibitor), Alk5i (TGF-β type I activin receptor-like kinase-4/-5/-7 inhibitor), ILV ((−)indolactam V), Ex-4 (exendin-4), NA (nicotinamide), IBMX (3-isobutyl-1-methylxanthine) and FRKL (forskolin).

Example 2: Differentiation into Pancreatic Progenitor Cells at High NOGGIN Concentrations The present inventors have attempted at developing a five-step protocol for the differentiation of hiPS cells into pancreatic hormone-expressing cells under xeno-free conditions by optimizing the protocol in a stepwise manner. Under the conditions as described in sub-section (3) in section (A) above, differentiation of undifferentiated hiPS cells into endocrine cells was performed. An outline of the 5-step differentiation protocol is shown in FIG. 2.

Figure 3:
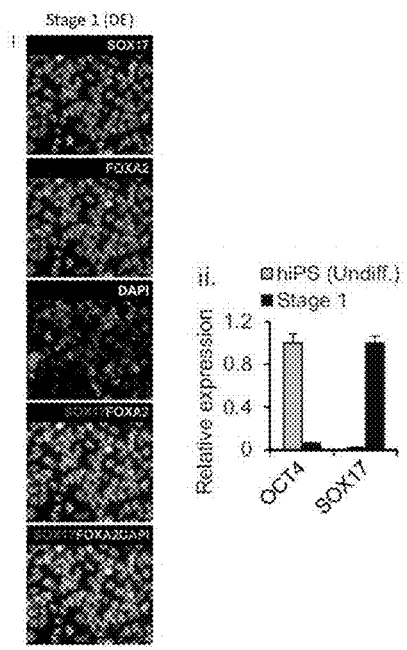
FIG. 3 The results of gene expression in differentiated cells at the end of step (1) (stage 1) are shown. Panel (i) shows SOX17/FOXA2-positive cells. Panel (ii) shows relative mRNA expression levels of DE markers between differentiated cells and undifferentiated hiPS cells. Scale bar=100 µm.

First, the present inventors attempted to prepare definitive endoderm cells (a layer of embryonic cells which yields the pancreas) under xeno-free conditions. At stage 1, hiPS cells were cultured in the presence of activin A and CHIR99021 (a GSK3β-specific inhibitor) for two days, followed by an additional three days of culture in the presence of activin A alone to induce differentiation into definitive endoderm (DE) cells. As shown in FIG. 3, at the end of stage 1, most cells differentiated into SOX17/FOXA2-double positive cells (71.7%±2.8% of the total cells) and expressed the transcript of a DE marker gene SOX17, whereas the expression level of a marker gene for undifferentiated hiPS cells, OCT4, was markedly decreased.

Figure 4:
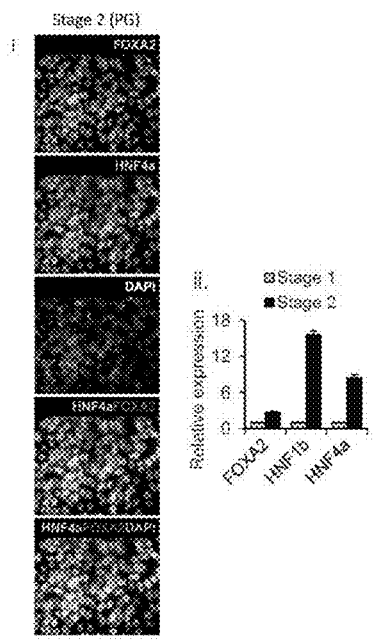
FIG. 4 The results of gene expression in differentiated cells at the end of step (2) (stage 2) are shown. Panel (i) shows HNF4a/FOXA2-positive cells. Panel (ii) shows relative mRNA expression levels of PG markers between cells at the end of step (1) and cells at the end of step (2). Scale bar=100 µm.

At stage 2, FGF10 and a hedgehog signaling inhibitor, KAAD-cyclopamine, were added and activin A was removed to thereby allow the transition into primitive gut tube (PG). As shown in FIG. 4, the present inventors detected a large proportion of HNF4a/FOXA2-double positive cells (77.7%±2.3% of the total cells) and upregulation of gut-tube marker genes FOXA2, HNF1b and HNF4a at the end of stage 2.

Figure 5:
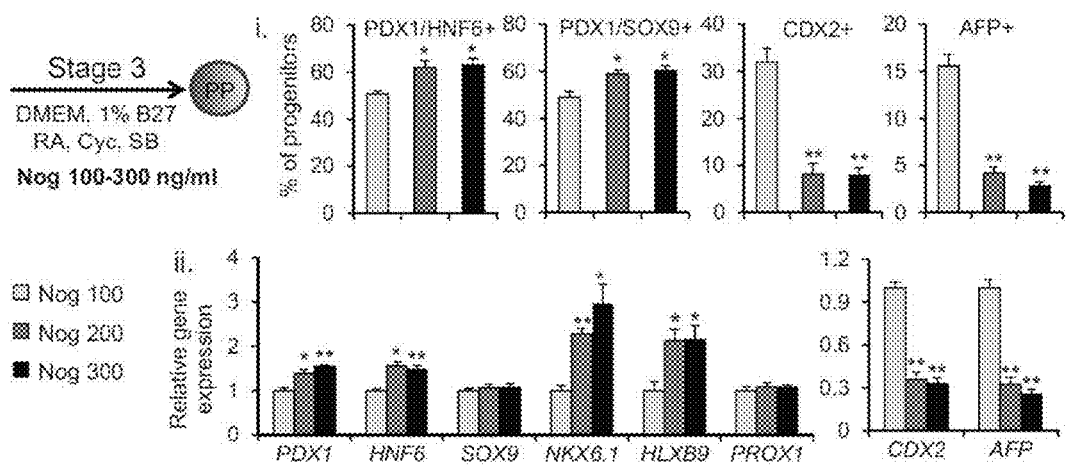
FIG. 5 The effect of NOGGIN addition on expression of each gene at step (3) (stage 3) is shown. Panel (i) shows percentages of PDX1/HNF6-, PDX1/SOX9-, CDX2- and AFP-positive cells. Panel (ii) shows relative mRNA expression levels of pancreatic, intestinal and hepatic progenitor cell markers at the end of step (3). In the analysis of gene expression, glyceraldehyde-3-phosphate dehydrogenase (GAPDH) was used as an internal RNA control. Mean±SEM (standard error of the mean) from three independent experiments (n=3) is presented. Student's t-tests were performed against the Nog 100 values: *p<0.05, **p<0.01.

At stage 3, combined treatment with retinoic acid (RA), KAAD-cyclopamine, SB431542 (SB; TGF-β type I activin receptor-like kinase-4/-5/-7 inhibitor), and NOGGIN (BMP signaling inhibitor) induced differentiation of PG cells into PDX1-positive pancreatic progenitor (PP) cells. Differentiated cells were generated by adding NOGGIN to the medium at 100, 200 and 300 ng/ml (Nog 100, Nog 200 and Nog 300). Expression of individual genes was confirmed by quantitative RT-PCR and immunocytochemistry. The results of quantitative RT-PCR are shown in FIG. 5, and the results of immunocytochemistry in FIG. 6. A considerable proportion of AFP-positive hepatic cells and CDX2-positive (mainly PDX1/CDX2-double positive) intestinal progenitor cells appeared when cells were treated with 100 ng/ml NOGGIN; their numbers were remarkably reduced when cells were treated with 200-300 ng/ml NOGGIN (FIG. 5, upper panels). Quantitative RT-PCR analysis also revealed that the gene expression levels of CDX2 and AFP were remarkably reduced at higher concentrations of NOGGIN, whereas the expression levels of PDX-1 and posterior foregut genes HNF6 and NKX6.1 were remarkably upregulated (FIG. 5, lower panels). The expression level of an early-stage pancreatic dorsal bud gene HLXB9 was also remarkably upregulated (FIG. 5, lower panels). These results suggest that BMP signal transduction inhibits differentiation into pancreatic lineages and that high NOGGIN concentrations cause differentiation into a high proportion of pancreatic progenitor cells.

Figure 6:
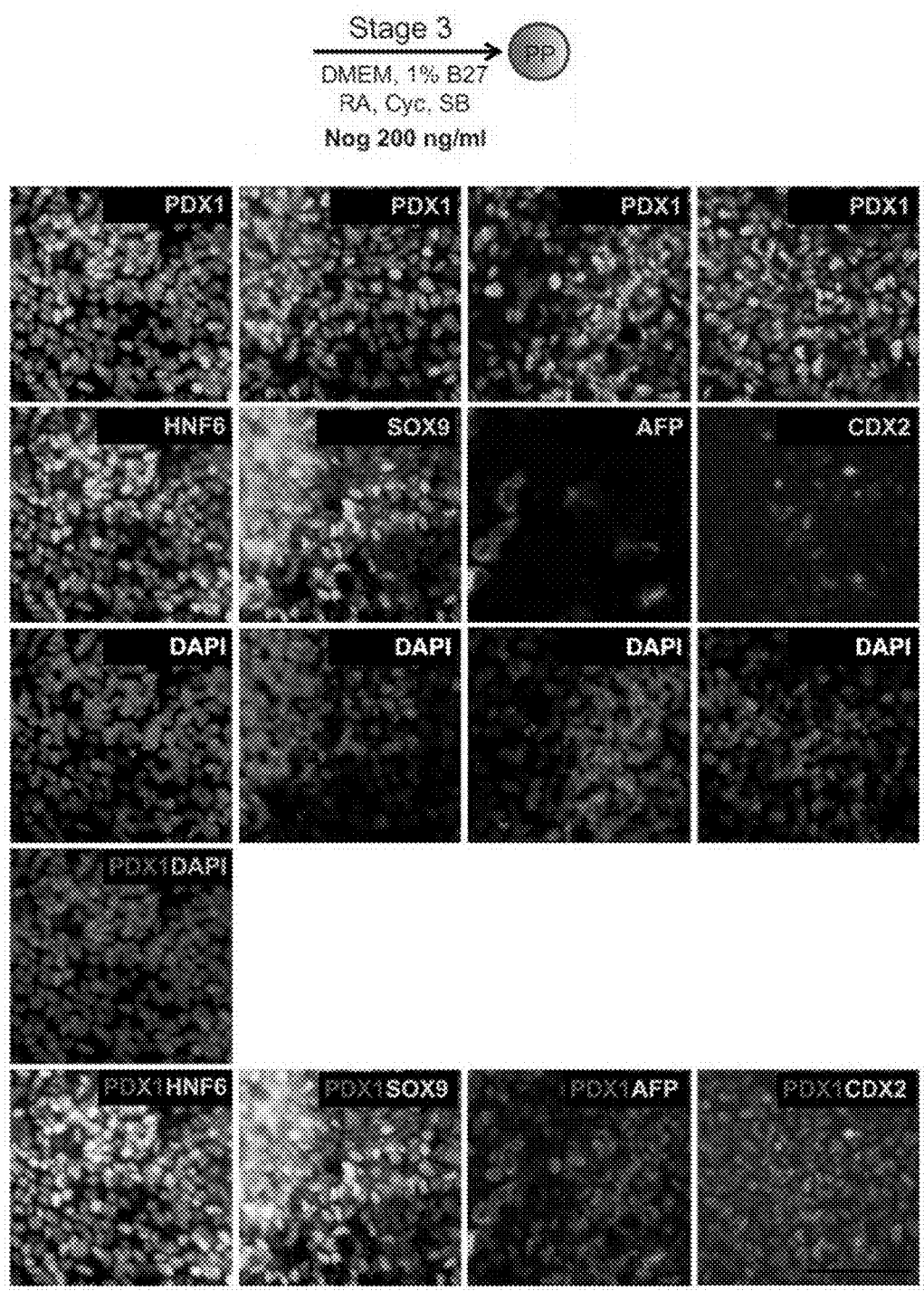
FIG. 6 The results of immunocytochemical analysis of the differentiated cells generated with addition of NOGGIN (200 ng/ml) at step (3) are shown. Expression patterns of PDX1—(red: pancreas), HNF6—(green: pancreas), SOX9—(green: pancreas), CDX2—(green: intestine) and AFP- (green: liver) positive cells are shown. Scale bar=100 µm.

When 200 ng/ml NOGGIN was added to stage-3 media, about 62% of PDX1-positive cells co-expressed HNF-6 and about 59% co-expressed SOX9, whereas only 8% of the cells were CDX2-positive and 4% of the cells were AFP-positive in the total DAPI-positive cells (FIG. 5, upper panels and FIG. 6). These results revealed that high NOGGIN concentrations induced differentiation into pancreatic cells while inhibiting differentiation into other cell lineages. This suggests that high NOGGIN concentrations efficiently induced differentiation into pancreatic progenitor cells.

Figure 7:
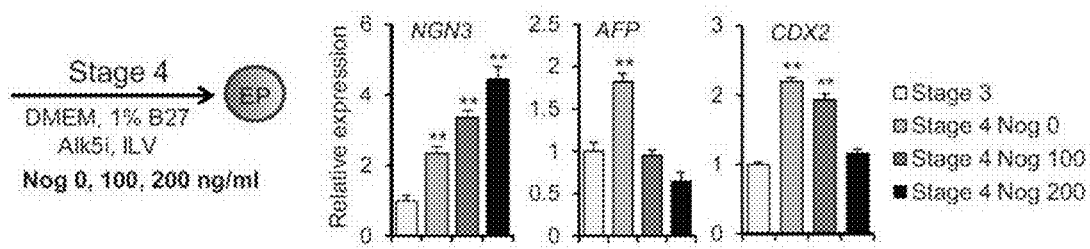
FIG. 7 Relative mRNA expression levels of NGN3, AFP and CDX2 in EP cells prepared in a medium containing NOGGIN at 0, 100 or 200 ng/ml (Nog 0, Nog 100, Nog 200) in addition to Alk5i and ILV at step (4) (stage 4) were analyzed by quantitative RT-PCR. The results compared with the results obtained from the cells of step (3) are shown. The results are presented as mean±SEM from three independent experiments (n=3). Student's t-tests were performed against the stage 3 values: *p<0.05, **p<0.01.
Figure 8:
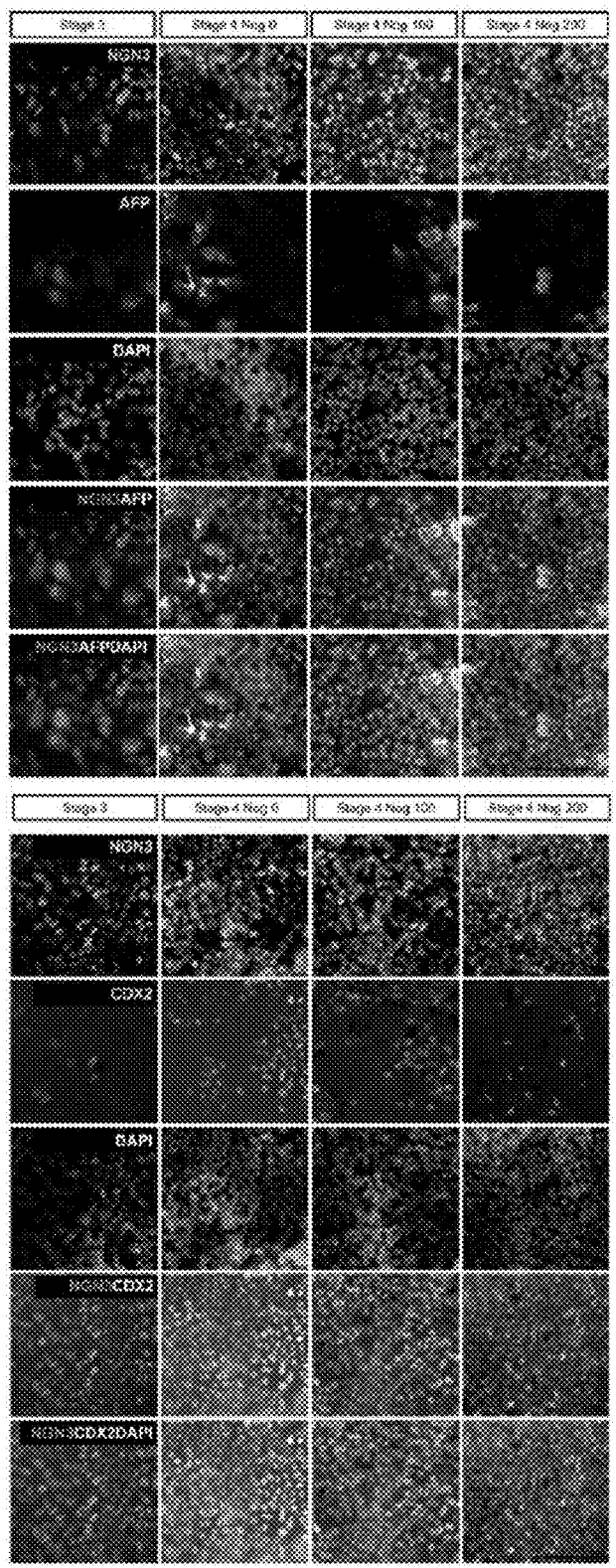
FIG. 8 The results of immunocytochemical analysis of the differentiated cells generated with Nog 0, Nog 100 and Nog 200 at step (4) are shown. Expression patterns of AFP-positive hepatic progenitor cells (green), CDX2-positive intestinal progenitor cells (green) and NGN3-positive endocrine progenitor cells (EP, red) are shown. Scale bar=100 µm.

Example 3: Differentiation of Cells into NGN3-Positive Pancreatic Endocrine Progenitor Cells at a High Ratio A previous study has reported that treatment with Alk5i (TGF-β type I activin receptor-like kinase-4/-5/-7 inhibitor), NOGGIN and protein kinase C activator promotes differentiation from pancreatic progenitor cells into endocrine progenitor (EP) cells (Non-Patent Document No. 5). The present inventors tested the differentiation from pancreatic progenitor cells into NGN3-positive endocrine progenitor cells using these factors in a xeno-free system. The expression of individual genes was confirmed by quantitative RT-PCR and immunocytochemistry. The results of quantitative RT-PCR are shown in FIG. 7, and the results of immunocytochemistry in FIGS. 8 and 9. When Alk5i, 200 ng/ml of NOGGIN and ILV (protein kinase C activator) were added to stage-4 medium, the expression of NGN3 transcript was remarkably upregulated, whereas AFP and CDX2 transcripts were maintained at the same levels as in stage-3 cells (FIG. 7). However, when no NOGGIN or low concentration NOGGIN was added to stage 4 medium, AFP and CDX2 transcripts were increased relative to the levels at stage 3, and AFP- and CDX2-positive cells appeared (FIGS. 7 and 8). It was shown that NOGGIN at 200 ng/ml was necessary for inducing differentiation of pancreatic progenitor cells into endocrine progenitor cells while inhibiting the re-appearance of AFP- and CDX2-positive cells.

Figure 9:
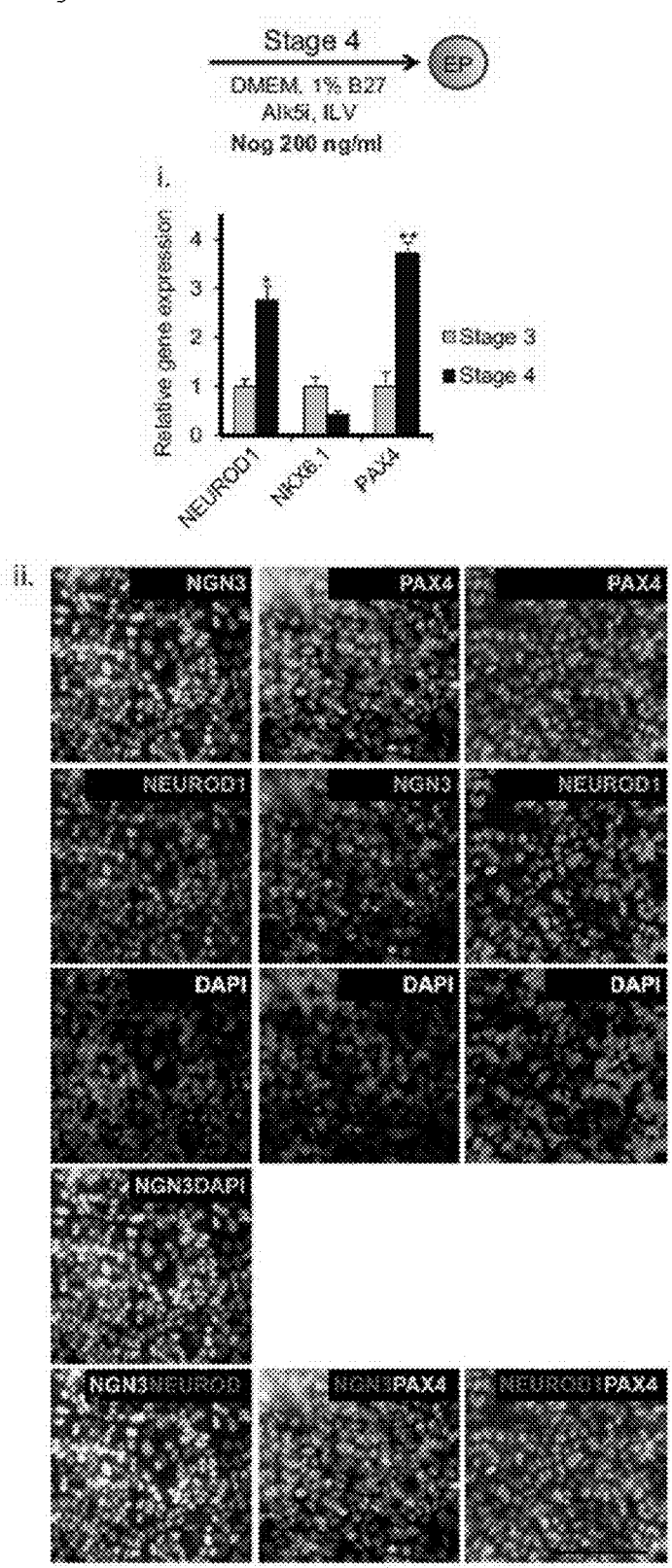
FIG. 9 This Figure shows gene expression of EP cell markers in the cells generated with Nog 200 at step (4). Panel (i) shows relative mRNA expression compared with that of step (3) cells. Panel (ii) shows the results of immunocytochemical analysis. Cells generated with Nog 200 at step (4) are showing co-expression of NGN3-positive cells (green or red) with NEUROD1 (red) and PAX4 (green). RNA transcript of GAPDH was used as an internal control. The results are presented as mean±SEM from three independent experiments (n=3). Student's t-tests were performed against the stage 3 values: *p<0.05, **p<0.01. Scale bar=100 µm.

At stage 4, the expression levels of transcripts of other endocrine progenitor cell genes (such as NEUROD1 and PAX4) were also remarkably increased (FIG. 9). The results of immunostaining showed that when treated with Alk5i, 200 ng/ml NOGGIN and ILV, 77.1 (±2.2)% of the cells expressed NGN3 and most of NGN3-positive cells co-expressed NEUROD1 and PAX4 (FIG. 9), reflecting a definite promise to differentiate into endocrine progenitor cell lineages.

Figure 10:
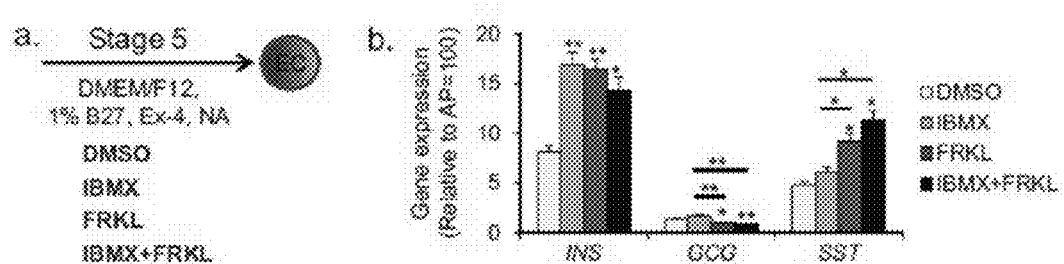
FIG. 10 Panel (a) shows a combination pattern of factors added to the basal medium (DMEM/F12, 1% B27, Ex-4 and NA) of step (5) (stage 5) to promote differentiation into pancreatic endocrine cells (EC). DMSO is a control. Panel (b) shows the result of quantitative RT-PCR analysis of relative mRNA expression levels of endocrine hormones insulin (INS), glucagon (GCG) and somatostatin (SST) in cells generated at the end of step (5) (stage 5). RNA transcript of GAPDH was used as an internal control. Gene expression levels were calculated taking the expression level of human adult pancreatic gene as 100. Mean±SEM from three independent experiments (n=3) is presented. Student's t-tests were performed against the DSMO values, unless otherwise indicated or performed between two discrete data sets: *p<0.05, **p<0.01. AP refers to adult pancreas.
Figure 11:
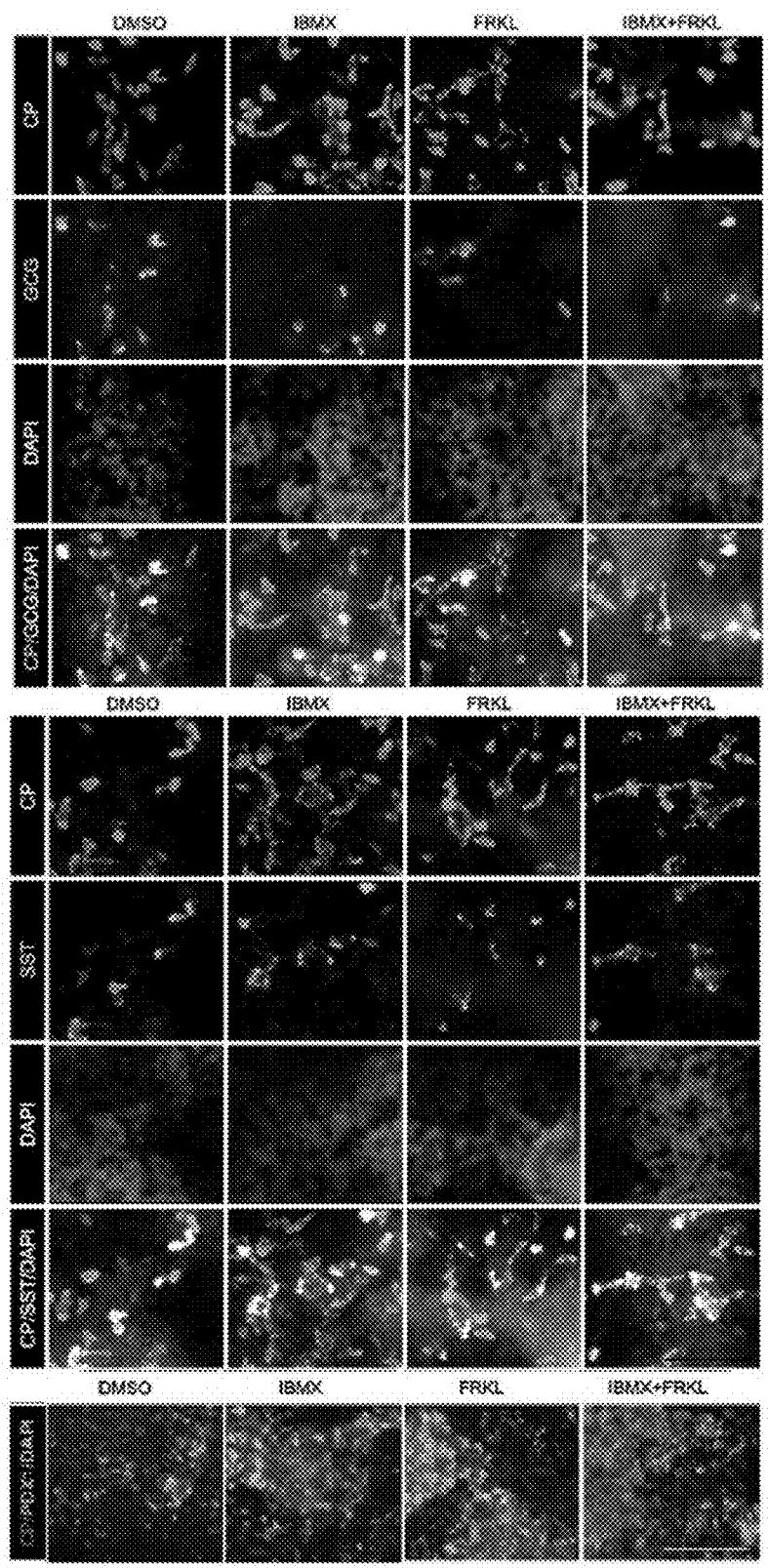
FIG. 11 The results of immunocytochemical analysis of hormone-positive cells generated at the end of step (5) are shown. C-peptide—(CP, red), GCG—(green), SST—(green) and PDX1—(green) positive cells are shown. Cells were counted after staining with DAPI (blue). Scale bar=100 µm.
Figure 12:
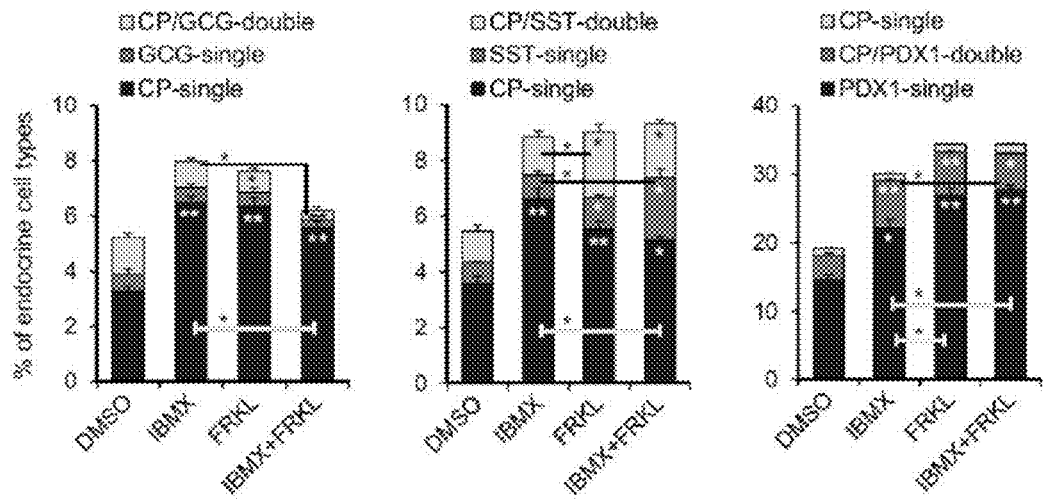
FIG. 12 The percentage of C-peptide—(CP), glucagon—(GCG), somatostatin—(SST) or PDX1-positive cells at the end of step (5) is shown.

Example 4: IBMX's Induction of Endocrine Progenitor Cells to Differentiate into Insulin-Positive Cells at a High Ratio Subsequently, the present inventors examined the differentiation of endocrine progenitor cells into insulin (INS)-expressing cells. At stage 5, exendin-4 (peptide agonist of GLP-1 receptor), nicotinamide, IBMX (phosphodiesterase inhibitor) and forskolin (FRKL, adenylate cyclase activator) were added to the medium. The expression of individual genes was confirmed by quantitative RT-PCR and immunocytochemistry. The results of quantitative RT-PCR are shown in FIG. 10, and the results of immunocytochemistry in FIGS. 11 and 12. The results of RT-PCR showed that differentiated cells expressed transcripts of INS, glucagon (GCG) and somatostatin (SST) but the expression level of GCG was very low compared to those of INS and SST under all conditions (FIG. 10). When IBMX, FRKL or both were added to the basal medium (DMEM/F12, 1% B27, exendin-4 and nicotinamide) at stage 5, INS expression was significantly upregulated. Immunostaining showed that 5%-8% of the differentiated cells were C-peptide (CP)-positive, the C-peptide being a byproduct of de novo insulin synthesis (FIGS. 11 and 12). Under all conditions, the proportion of GCG single-positive cells (approximately 0.3-0.6%) or CP/GCG-double positive cells (approximately 0.3-1.4%) was very low. The proportion of SST dingle-positive (approximately 0.75-2.25%) or CP/SST double-positive cells (approximately 1.2-2.4%) was higher than that of GCG-positive cells. Among cells treated with IBMX, FRKL or both, the proportions of CP single-positive cells were approximately 6.5-6.7%, approximately 5.6-6.4% and approximately 5.1-5.6%, each of which was significantly higher than the proportion (approximately 3.2-3.6%) treated with control DMSO (FIGS. 11 and 12). The proportions of CP/SST double-positive cells and SST single-positive cells were higher in KFRL-treated and IBMX+KFRL-treated cells than in DMSO-treated cells. The proportion of CP/SST double-positive cells in FRKL-treated cells and the proportion of SST single-positive cells in IBMX+KFRL-treated cells were significantly higher than those proportions in DSMO-treated cells (FIGS. 11 and 12).

The results of immunostaining also showed significantly high proportions of PDX1-positive/CP-negative cells in IBMX-treatment (approximately 22%), FRKL-treatment (approximately 27%) and IBMX+FRKL-treatment (approximately 28%) compared to the corresponding proportion in DMSO-treatment (approximately 15%). Most of the PDX1-positive/CP-negative cells were observed in a monolayer and not in clustered structures, indicating that they may be immature cells at the pancreatic progenitor stage. Under all culture conditions used, only very few cells were pancreatic polypeptide-positive or amylase-positive.

Figure 13:
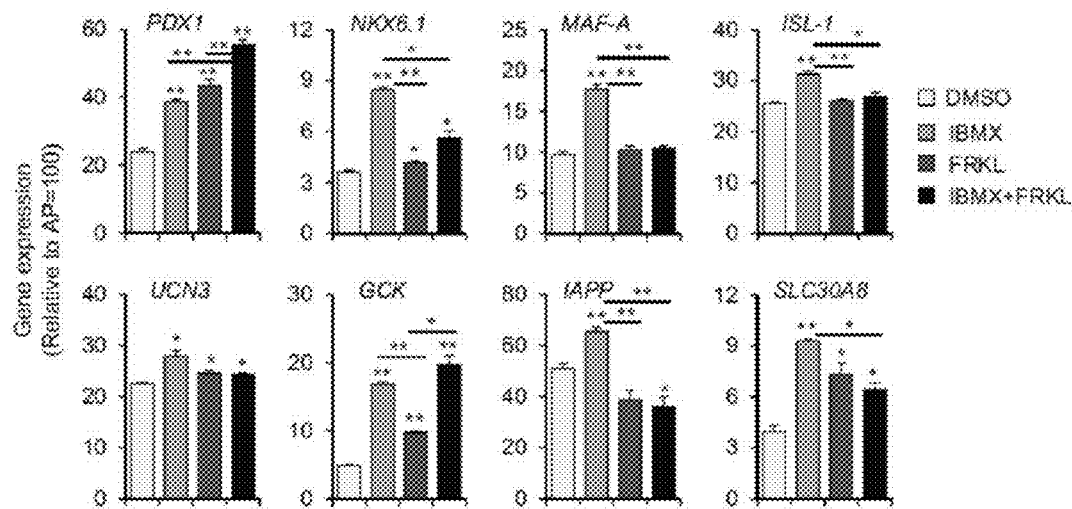
FIG. 13 The results of quantitative RT-PCR analysis of relative expression of 13 cell-specific genes in differentiated cells generated at the end of step (5) (stage 5) are shown. RNA transcript of GAPDH was used as an internal control. Gene expression levels were calculated taking the expression level of human adult pancreatic gene as 100. Mean±SEM from three independent experiments (n=3) is presented. Student's t-tests were performed against the DSMO values unless otherwise indicated: *p<0.05, **p<0.01. AP refers to adult pancreas.

Next, the present inventors evaluated the mRNA expression levels of β-cell specific markers such as PDX1, NKX6.1, MAF-A, ISL-1, urocortin-3 (UCN3), glucokinase (GCK), islet amyloid polypeptide (IAPP) and SLC30A8, in cells cultured under all four conditions by quantitative RT-PCR. The results are shown in FIG. 13. The results showed that the expression levels of these β-cell maturity genes were remarkably higher in IBMX-induced differentiated cells than in DMSO-induced cells under all conditions.

Figure 14:
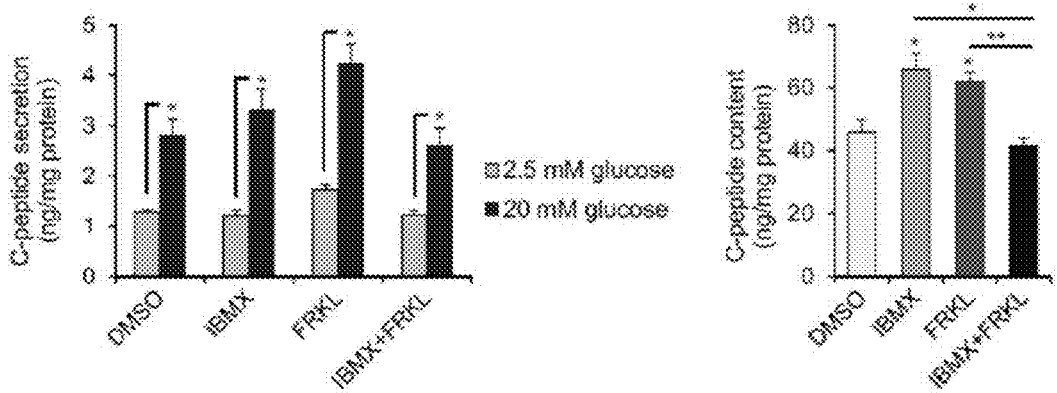
FIG. 14 Left panel shows the result of ELISA analysis of in vitro glucose-stimulated C-peptide secretion in differentiated cells at the end of step (5). C-peptide secretion levels under stimulation with 20 mM glucose were compared with those detected under treatment with 2.5 mM glucose. Right panel shows C-peptide contents in differentiated cells at the end of step (5). Mean±SEM from three independent experiments (n=3) is presented. Student's t-tests were performed against the 2.5 mM glucose values: *p<0.05, **p<0.01.

Then, C-peptide secretion in response to glucose was assessed in differentiated cells. Only marginal amounts of C-peptide signals were detected at an extracellular glucose level of 2.5 mM (mimicking fasting state). The results are shown in FIG. 14. In contrast, C-peptide secretion was significantly increased under all culture conditions in response to 20 mM glucose (2.1-2.7-fold over basal level). The inventors also detected intracellular C-peptide contents in cells under all four conditions; the levels were significantly higher in IBMX-induced (approximately 66 ng/mg protein) and FRKL-induced (approximately 62 ng/mg protein) cells than in DMSO-induced cells (approximately 46 ng/mg protein). The results are shown in FIG. 14, right panel. These results support the presence of C-peptide pools in the differentiated cells.

Figure 15:
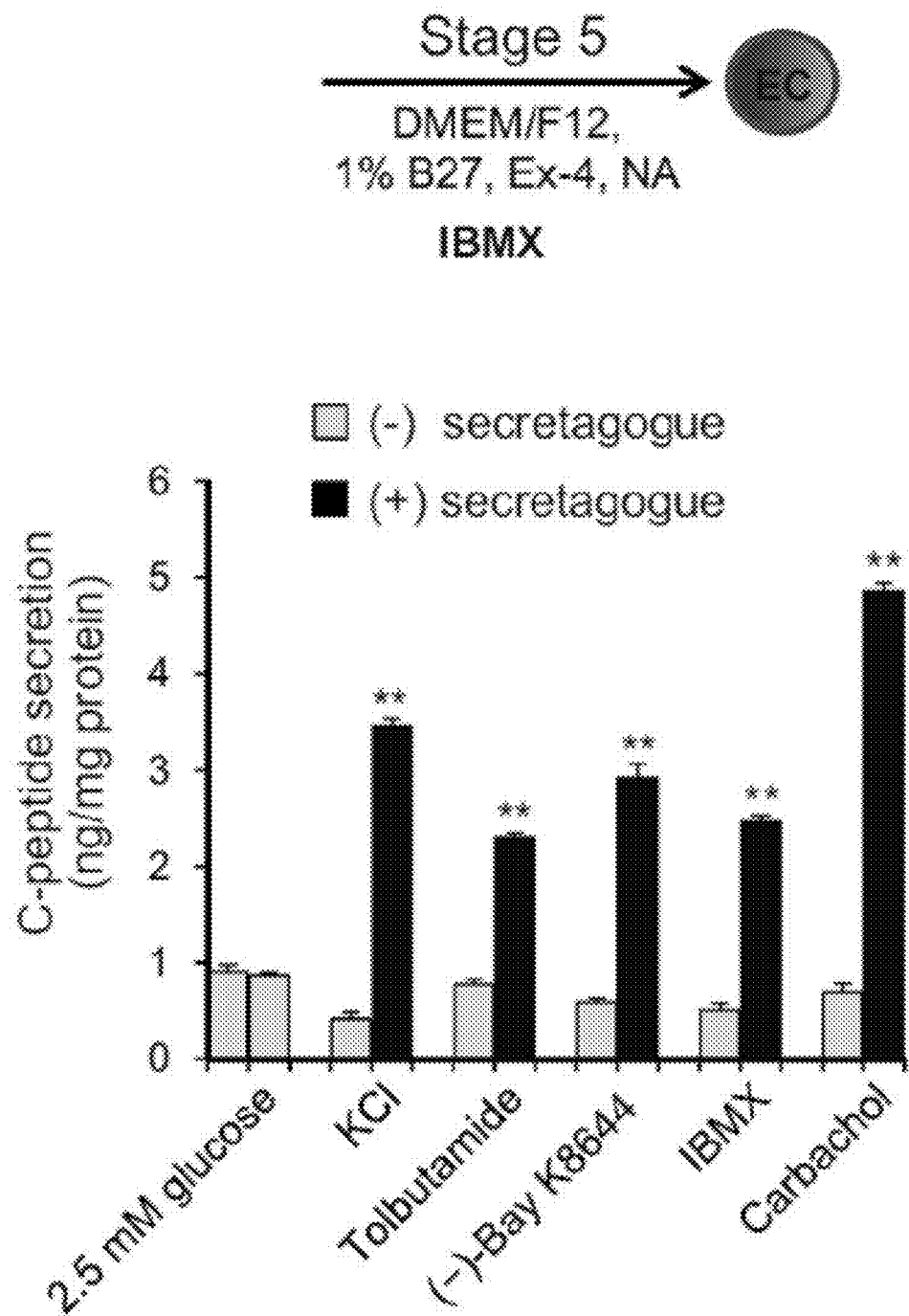
FIG. 15 In vitro C-peptide secretion levels in response to various insulin secretagogues in differentiated cells at the end of step (5) are shown. C-peptide secretion levels under treatment with secretagogues were compared with those detected under 2.5 mM glucose treatment without secretagogues. The results are shown as mean±SEM from three independent experiments (n=3). Student's t-tests were performed against the values of 2.5 mM glucose without secretagogues: *p<0.05, **p<0.01.
Figure 16:
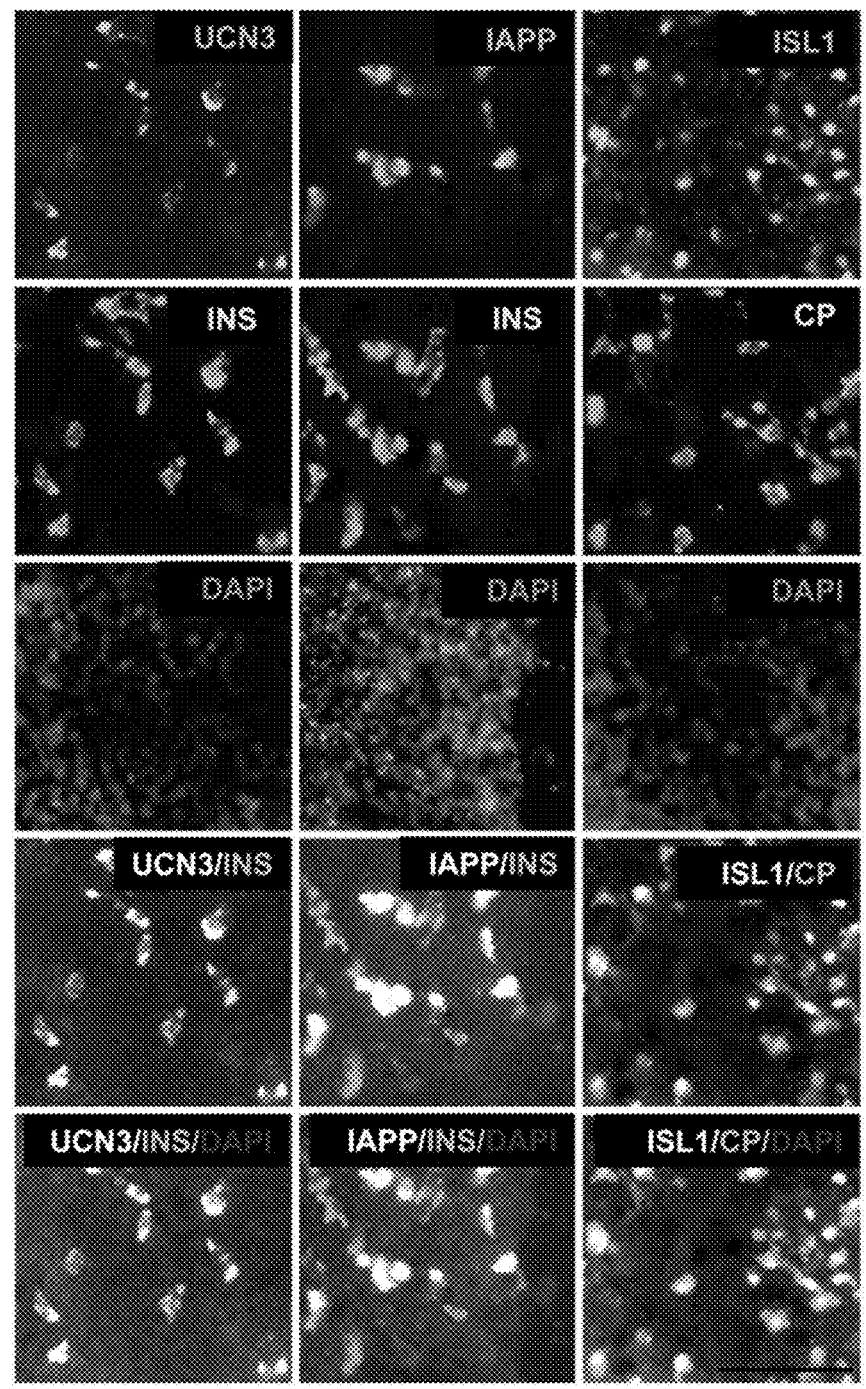
FIG. 16 Co-expression of β-cell maturation markers and INS/CP-positive cells is shown. Most of INS/CP-positive cells (red) were co-expressed with β-cell maturation markers such as UCN3 (green), IAPP (green), ISL-1 (green), etc. Cells were counter-stained with DAPI (blue). The uppermost panel shows UCN3, IAPP or ISL1 staining (green). The right panel shows merged images. Scale bar=100 μm.

Example 5: Maturity Characteristics of In Vitro-Generated INS-Expressing Cells To further confirm the mature β-cell characteristics of the induced INS-expressing cells, the present inventors assessed C-peptide secretion in differentiated cells in response to various insulin secretagogues. The results are shown in FIG. 15. Direct depolarization of the cells by addition of potassium chloride (KCl) increased C-peptide secretion in 1 hr incubation approximately 8.3-fold. The presence of intracellular functional KATP channels is supported by the result that C-peptide secretion increased to approximately 3.0-fold relative to the standard level where tolbutamide, a KATP channel blocker, was added. Treatment with (−) BAY K8644, an L-type VDDC agonist, stimulated C-peptide secretion to approximately 4.9-fold, suggesting functional activation of VDCC(s). Further, the present inventors assessed cellular responsivity to cAMP which affects insulin secretion. Increasing the cAMP level using IBMX (phosphodiesterase inhibitor) resulted in increase of C-peptide secretion by approximately 4.9-fold. Moreover, treatment of cells with carbachol (a muscarinic agonist) also increased the secretion of C-peptide by approximately 7.0-fold. The results are shown in FIG. 15. Immunocytochemical analysis also demonstrated that a large number of INS-positive or CP-positive cells were co-expressing β-cell maturity markers UROCORTIN-3 (UCN3), IAPP and ISL1. The results are shown in FIG. 16. Taken together, these results suggest that the INS-expressing cells induced during culture were functionally matured.

Figure 17:
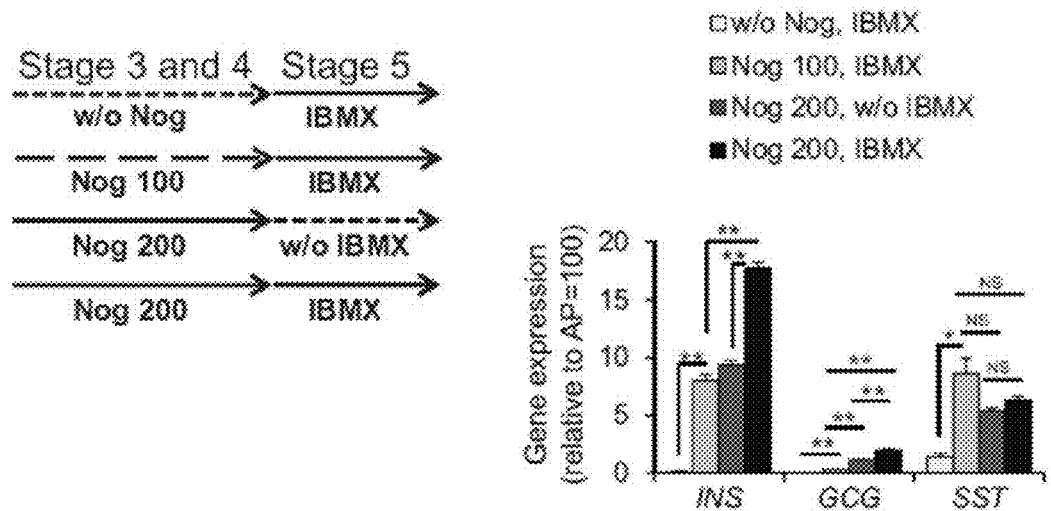
FIG. 17 Left panel shows a schematic drawing of pancreatic differentiation procedures using various combinations of NOGGIN (w/o Nog, Nog 100 and Nog 200 ng/ml with other components) at steps (3) and (4) and IBMX at step (5) (basal medium with or without IBMX). Right panel shows the results of quantitative RT-PCR analysis of relative mRNA expression levels of INS, GCG and SST in differentiated cells at the end of step (5). RNA transcript of GAPDH was used as an internal control. Gene expression levels were calculated taking the expression level of human adult pancreatic gene as 100. Mean±SEM from three independent experiments (n=3) is presented. Student's t-tests were performed between two discrete data sets: *p<0.05, **p<0.01. AP refers to adult pancreas.

Example 6: Effect of NOGGIN and IBMX on Differentiation from hiPS-Derived Cells into INS-Expressing Cells The present inventors examined the key factors that properly direct hiPS-derived cells to differentiate into INS single-positive cells, and found that NOGGIN and IBMX cooperatively enhanced differentiation from hiPS-derived cells into INS-expressing cells. Only when the inventors added 200 ng/ml of NOGGIN (Nog 200) at stages 3 and 4 and IBMX at stage 5, expression of INS transcript was significantly upregulated, whereas hiPS-derived cells expressed INS only at a very low level in the absence of NOGGIN (FIG. 17).

Figure 18:
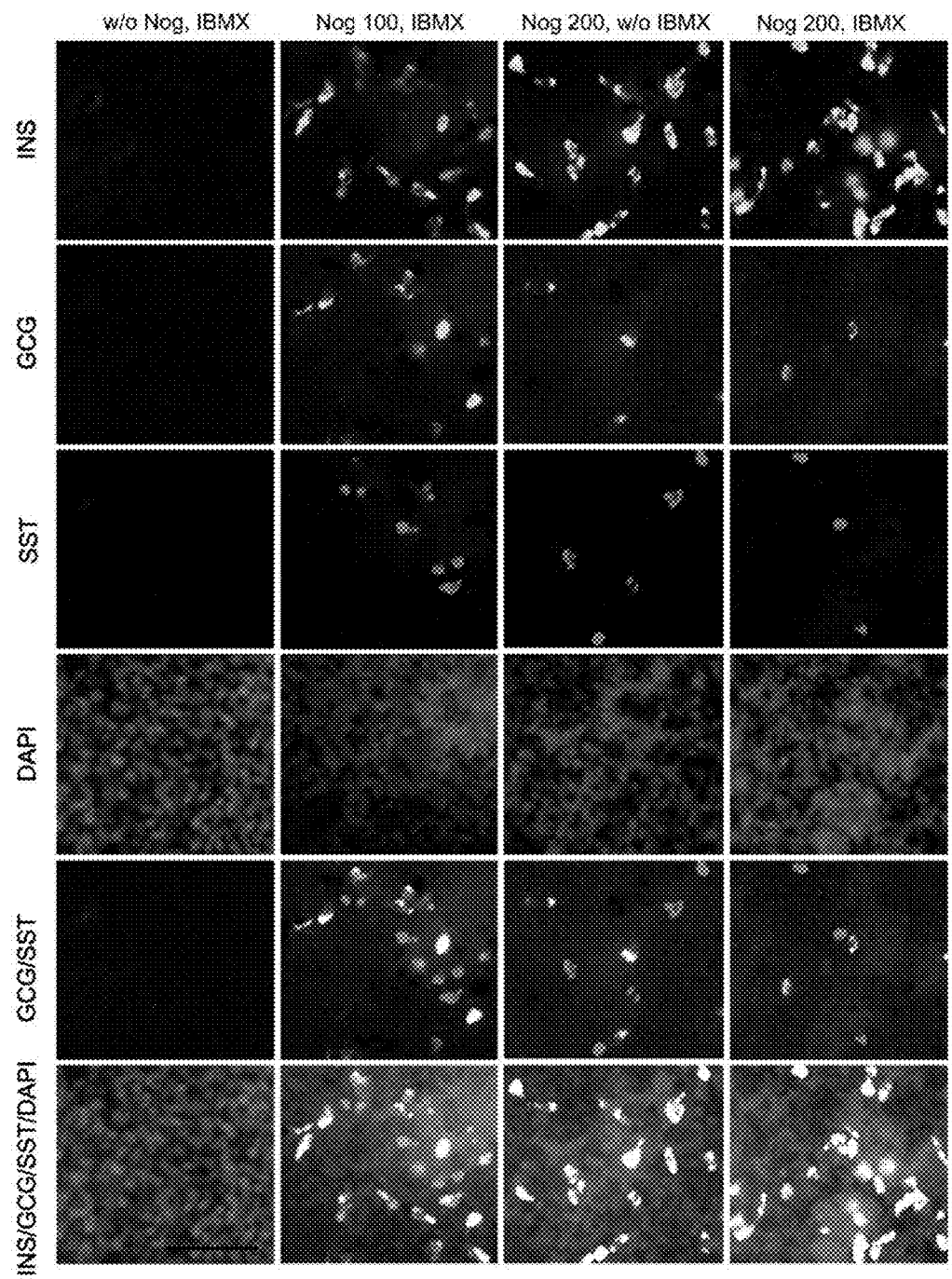
FIG. 18 Expression patterns of INS (green), GCG (cyan) and SST (red) in differentiated cells at the end of step (5) are shown. Scale bar=100 μm.
Figure 19:
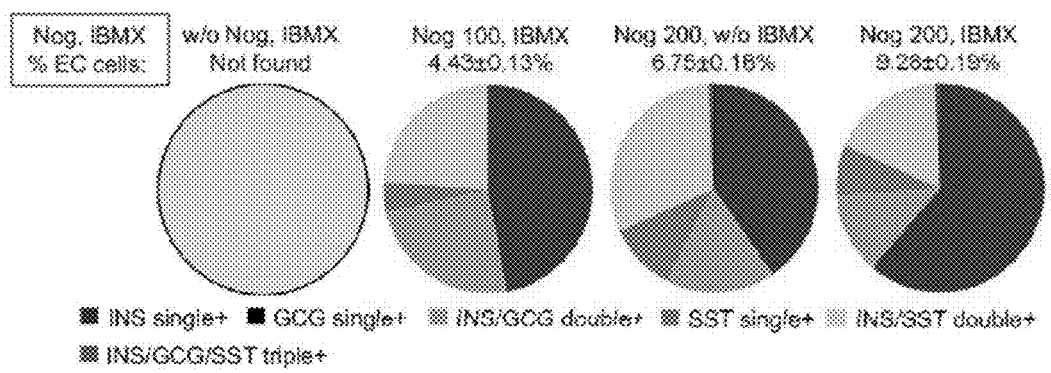
FIG. 19 Relative percentages of INS-, GCG- and SST-positive sub-populations in differentiated cells at the end of step (5) are shown. Individual percentages of pancreatic endocrine cells among all DAPI-positive cells are shown.
Figure 20:
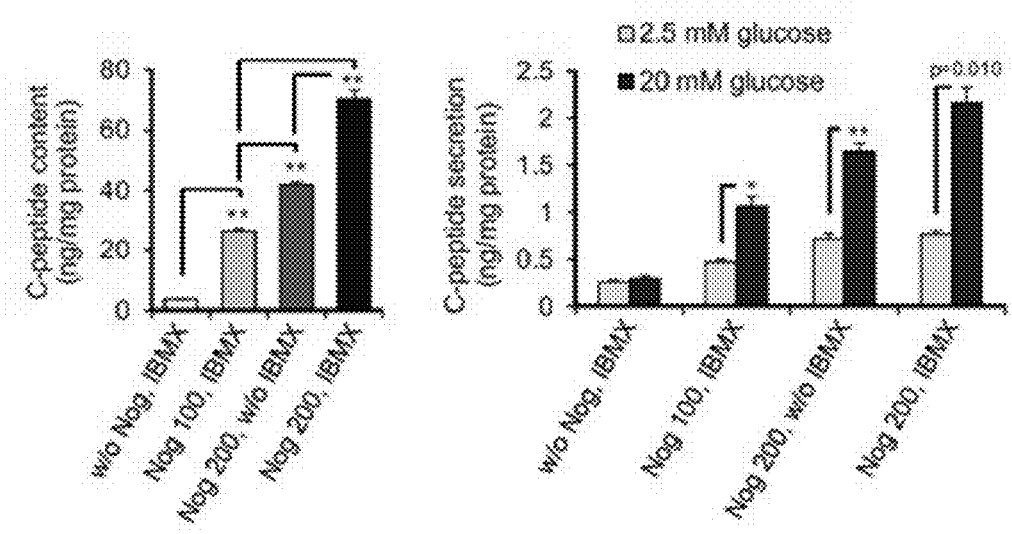
FIG. 20 Left panel shows endogenous C-peptide contents in differentiated cells generated at the end of step (5). Right panel shows in vitro glucose-stimulated C-peptide secretion in differentiated cells at the end of step (5). Secretion levels of C-peptide under 20 mM glucose stimulation were compared with those levels detected under 2.5 mM glucose treatment. Results are shown as mean±SEM (n=3). Student's t-tests were performed against the 2.5 mM glucose values: *p<0.05, **p<0.01.
Figure 21:
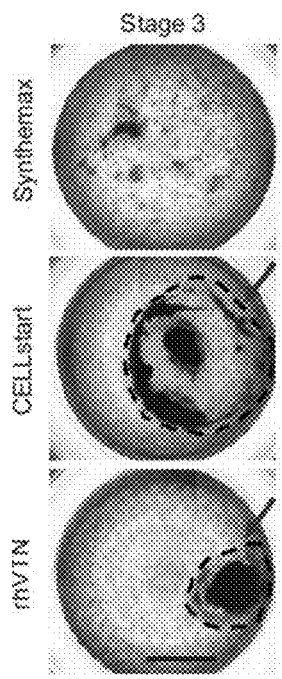
FIG. 21 Bright field microscopic photographs of cell culture images at the end of step (3) are shown. The cells were differentiated under xeno-free conditions using xeno-free scaffolds (Synthemax, CELLstart and rhVTN). Arrows indicate those cells forming a large mass. Scale bar=5 mm.

The results of immunohistochemical analysis showed that INS-positive cells were hardly detected in the absence of NOGIN but addition of NOGGIN at 200 ng/ml produced a higher proportion of EC cells compared to addition of NOGGIN at 100 ng/ml (FIGS. 18 and 19). Addition of IBMX and NOGGIN at 200 ng/ml further increased the proportion of INS single-positive cells. When IBMX and high concentration NOGGIN (200 ng/ml) are used in the directed differentiation step, C-peptide content and GSIS activity were also increased significantly (FIG. 21). The above results support the hypothesis that NOGGIN and IBMX cooperatively promote and regulate the differentiation of hiPS-derived cells into INS-producing cells.

Figure 22:
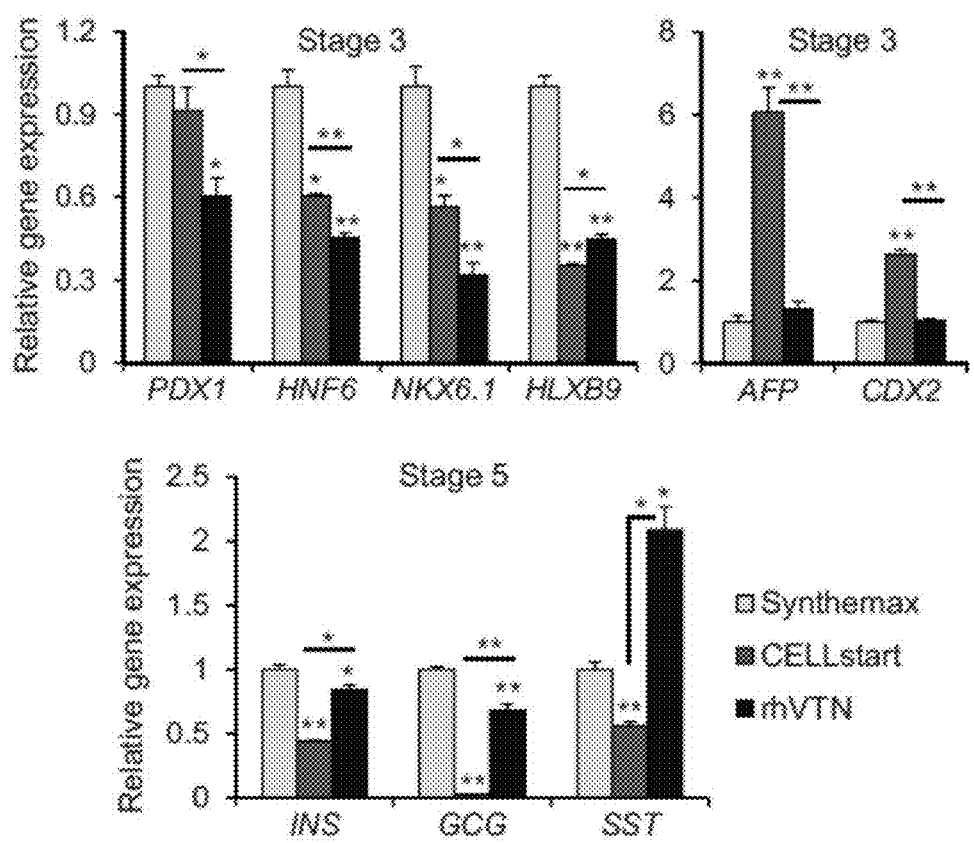
FIG. 22 Expression levels of marker genes in differentiated cells at the end of step (3) and step (5) are shown. RNA transcript of GAPDH was amplified as an internal control. The results are shown as mean±SEM (n=3). Student's t-tests were performed against the Synthemax values. Significant difference was *p<0.05, **p<0.01.

Example 7: Confirmation of Xenogeneic Contamination in In Vitro-Generated INS-Expressing Cells The present inventors evaluated the degree of non-human-derived contamination in differentiated cells by detecting the expression of Neu5Gc. Flow cytometry showed that the expression of Neu5Gc was below the detection limit at the ends of stage 4 and stage 5 when xeno-free culture conditions were used, indicating that the directed differentiation system used in the present invention is xeno-free. The present inventors also examined pancreatic differentiation on other commercially available xeno-free scaffolds. It was observed that the cells detached from CELLstart (comprising fibronectin) and rhVTN matrix formed large clumps (FIG. 21). Therefore, CELLstart and rhVTN were less suitable than Synthemax for long-term differentiation culture. Moreover, Synthemax was also superior to CELLstart or rhVTN on differentiation efficiency into pancreatic lineages, as indicated by significantly higher expression levels of PDX1, HNF6, NKX6.1, HLXB9 and INS genes, and significantly lower expression levels of AFP and CDX2 genes (FIG. 22).

As described above, the present inventors have established for the first time a defined xeno-free culture system to induce insulin-expressing β-cells from hiPS cells, using a synthetic scaffold and a serum-free medium comprising humanized and/or recombinant supplements and growth factors. The present inventors have demonstrated that combined use of NOGGIN (a BMP signaling inhibitor) and IBMX (a phosphodiesterase inhibitor) directs hiPS-derived cells to differentiate into functionally matured INS-expressing cells which exhibit C-peptide secretion in response to various insulin-secretagogues and high glucose levels and express several markers of functionally matured β-cells.

What has been described so far is intended to solely explain the objects and the subjects of the present invention and is not intended to limit the scope of claim attached hereto. Various alterations and substitutions to the embodiments disclosed without departing from the scope of claim attached hereto are obvious for one of ordinary skill in the art from the teachings disclosed in the present specification.

INDUSTRIAL APPLICABILITY

According to the method of directed differentiation of the present invention, it is possible to efficiently direct pluripotent cells (e.g., ES cells or iPS cells) to differentiate into insulin-producing cells. The insulin-producing cells obtained by this method of directed differentiation may be used for screening for compounds useful for prevention and/or treatment of diseases such as diabetes.

---

The invention claimed is:

1. A method for directed differentiation into insulin-producing cells, comprising culturing endodermal cells in the following steps (a) to (d):
   (a) culturing the endodermal cells in a medium comprising a hedgehog signaling inhibitor and an FGF;
   (b) culturing the cells obtained in step (a) in a medium comprising a retinoic acid receptor agonist, a hedgehog signaling inhibitor and noggin;
   (c) culturing the cells obtained in step (b) in a medium comprising a TGF-β type I activin receptor-like kinase-4/-5/-7 inhibitor and noggin; and
   (d) culturing the cells obtained in step (c) in a medium comprising GLP-1 receptor agonist and nicotinamide to produce insulin-producing cells,
   wherein the concentration of the noggin in steps (b) and (c) is at least 200 ng/ml or more.

2. The method of claim 1, wherein the concentration of the noggin in steps (b) and (c) is 200-500 ng/ml.

3. The method of claim 1, wherein step (c) further comprises a protein kinase C activator.

4. The method of claim 1, wherein the retinoic acid receptor agonist in step (b) is retinoic acid and the hedgehog signaling inhibitor in steps (a) and (b) is KAAD-cyclopamine.

5. The method of claim 3, wherein the protein kinase C activator is indolactam V.

6. The method of claim 1, which is characterized by conducting all of the steps (a) to (d) in a xeno-free culture system.

7. The method of claim 1, wherein the endodermal cells are differentiated from pluripotent stem cells or embryonic stem cells.

8. The method of claim 1, further comprising, before step (a), (1-1) culturing human or mouse pluripotent stem cells in a medium comprising an activator of activing receptor-like kinase-4/-7 and a GSK3 inhibitor and then (1-2) culturing in a medium comprising an activator of activing receptor-like kinase-4/-7 to effect differentiation into endodermal cells.

9. The method of claim 8, wherein the medium in step (1-2) does not comprise a GSK3 inhibitor.

10. The method of claim 8, all of the steps (1-1) to (d) are in a xeno-free culture system.

11. The method of claim 1, wherein the hedgehog signaling inhibitor is SANT-1.

12. The method of claim 1, wherein FGF is FGF10.

13. The method of claim 1, wherein the BMP signaling inhibitor is LDN193189.

14. The method of claim 1, wherein the retinoic acid receptor agonist is retinoic acid.

15. The method of claim 1, wherein the TGF-β type I activin receptor-like kinase-4/-5/-7 inhibitor is Alk5 inhibitor.

16. The method of claim 1, wherein the GLP-1 receptor agonist is exendin-4.

17. The method of claim 1, further comprising isolating the cells from step (d).

18. The method of claim 1, wherein the medium of step (d) excludes a growth factor.

19. A method for directed differentiation into mature insulin-producing cells, comprising culturing endodermal cells in the following steps (a) to (d):
   (a) culturing the endodermal cells in a medium comprising SANT-1 and FGF10;
   (b) culturing the cells obtained in step (a) in a medium comprising retinoic acid, SANT-1 and noggin;
   (c) culturing the cells obtained in step (b) in a medium comprising Alk5 inhibitor, noggin, and indolactam V; and
   (d) culturing the cells obtained in step (c) in a medium comprising nicotinamide and exendin-4 to produce insulin-producing cells,
   wherein the concentration of the noggin in steps (b) and (c) is at least 200 ng/ml or more.

20. A method for directed differentiation into mature insulin-producing cells, the method consisting of:
   (a) culturing human or mouse pluripotent stem cells in a medium comprising an activator of activing receptor-like kinase-4/-7 and a GSK3 inhibitor;
   (b) culturing the cells of step (a) in a medium comprising an activator of activing receptor-like kinase-4/-7 to effect differentiation into endodermal cells;
   (c) culturing the endodermal cells of step (b) in a medium comprising a hedgehog signaling inhibitor and an FGF;
   (d) culturing the cells obtained in step (c) in a medium comprising a retinoic acid receptor agonist, a hedgehog signaling inhibitor and a BMP signaling inhibitor;
   (e) culturing the cells obtained in step (d) in a medium comprising a TGF-β type I activin receptor-like kinase-4/-5/-7 inhibitor and a BMP signaling inhibitor; and
   (f) culturing the cells obtained in step (e) in a medium comprising GLP-1 receptor agonist and nicotinamide to produce insulin-producing cells.

21. The method of claim 19, wherein the concentration of noggin in steps (b) and (c) is 200-500 ng/ml.

22. The method of claim 20, wherein the endodermal cells are differentiated from pluripotent stem cells or embryonic stem cells.

* * * * *

SEQUENCE LISTING

<160> NUMBER OF SEQ ID NOS: 60

<210> SEQ ID NO 1
<211> LENGTH: 20
<212> TYPE: DNA
<213> ORGANISM: Artificial Sequence

```
<220> FEATURE:
<223> OTHER INFORMATION: primer for GAPDH

<400> SEQUENCE: 1
cgagatccct ccaaaatcaa                                              20

<210> SEQ ID NO 2
<211> LENGTH: 21
<212> TYPE: DNA
<213> ORGANISM: Artificial Sequence
<220> FEATURE:
<223> OTHER INFORMATION: primer for OCT3/4

<400> SEQUENCE: 2
gtattcagcc aaacgaccat c                                            21

<210> SEQ ID NO 3
<211> LENGTH: 21
<212> TYPE: DNA
<213> ORGANISM: Artificial Sequence
<220> FEATURE:
<223> OTHER INFORMATION: primer for CER1

<400> SEQUENCE: 3
gccgatagat ggaatgaaaa t                                            21

<210> SEQ ID NO 4
<211> LENGTH: 21
<212> TYPE: DNA
<213> ORGANISM: Artificial Sequence
<220> FEATURE:
<223> OTHER INFORMATION: primer for SOX17

<400> SEQUENCE: 4
gctttcatgg tgtgggctaa g                                            21

<210> SEQ ID NO 5
<211> LENGTH: 22
<212> TYPE: DNA
<213> ORGANISM: Artificial Sequence
<220> FEATURE:
<223> OTHER INFORMATION: primer for FOXA2

<400> SEQUENCE: 5
ctgagcgaga tctaccagtg ga                                           22

<210> SEQ ID NO 6
<211> LENGTH: 21
<212> TYPE: DNA
<213> ORGANISM: Artificial Sequence
<220> FEATURE:
<223> OTHER INFORMATION: primer for HNF16

<400> SEQUENCE: 6
atagctccaa ccagactcac a                                            21

<210> SEQ ID NO 7
<211> LENGTH: 22
<212> TYPE: DNA
<213> ORGANISM: Artificial Sequence
<220> FEATURE:
<223> OTHER INFORMATION: primer for HNF4a

<400> SEQUENCE: 7
ccaagagatc catggtgttc aa                                           22
```

```
<210> SEQ ID NO 8
<211> LENGTH: 23
<212> TYPE: DNA
<213> ORGANISM: Artificial Sequence
<220> FEATURE:
<223> OTHER INFORMATION: primer for PDX1

<400> SEQUENCE: 8
cttggaaacc aacaactatt cac                                            23

<210> SEQ ID NO 9
<211> LENGTH: 20
<212> TYPE: DNA
<213> ORGANISM: Artificial Sequence
<220> FEATURE:
<223> OTHER INFORMATION: primer for HNF6

<400> SEQUENCE: 9
aaatcaccat ttcccagcag                                                20

<210> SEQ ID NO 10
<211> LENGTH: 20
<212> TYPE: DNA
<213> ORGANISM: Artificial Sequence
<220> FEATURE:
<223> OTHER INFORMATION: primer for NKX6.1

<400> SEQUENCE: 10
ccaagaagaa gcaggactcg                                                20

<210> SEQ ID NO 11
<211> LENGTH: 23
<212> TYPE: DNA
<213> ORGANISM: Artificial Sequence
<220> FEATURE:
<223> OTHER INFORMATION: primer for SOX9

<400> SEQUENCE: 11
aaaggcaact cgtacccaaa ttt                                            23

<210> SEQ ID NO 12
<211> LENGTH: 27
<212> TYPE: DNA
<213> ORGANISM: Artificial Sequence
<220> FEATURE:
<223> OTHER INFORMATION: primer for PROX1

<400> SEQUENCE: 12
aaagcaaagc tcatgttttt ttatacc                                        27

<210> SEQ ID NO 13
<211> LENGTH: 20
<212> TYPE: DNA
<213> ORGANISM: Artificial Sequence
<220> FEATURE:
<223> OTHER INFORMATION: primer for HLXB9

<400> SEQUENCE: 13
gcaccagttc aagctcaaca                                                20

<210> SEQ ID NO 14
<211> LENGTH: 20
<212> TYPE: DNA
<213> ORGANISM: Artificial Sequence
<220> FEATURE:
<223> OTHER INFORMATION: primer for CDX2
```

```
<400> SEQUENCE: 14
ctcctcccca gctcttctct                                               20

<210> SEQ ID NO 15
<211> LENGTH: 20
<212> TYPE: DNA
<213> ORGANISM: Artificial Sequence
<220> FEATURE:
<223> OTHER INFORMATION: primer for AFP

<400> SEQUENCE: 15
tgccaactca gtgaggacaa                                               20

<210> SEQ ID NO 16
<211> LENGTH: 20
<212> TYPE: DNA
<213> ORGANISM: Artificial Sequence
<220> FEATURE:
<223> OTHER INFORMATION: primer for NGN3

<400> SEQUENCE: 16
tcgagagaga gcgtgacaga                                               20

<210> SEQ ID NO 17
<211> LENGTH: 20
<212> TYPE: DNA
<213> ORGANISM: Artificial Sequence
<220> FEATURE:
<223> OTHER INFORMATION: primer for PAX4

<400> SEQUENCE: 17
cagactgtgg ctccttcctc                                               20

<210> SEQ ID NO 18
<211> LENGTH: 20
<212> TYPE: DNA
<213> ORGANISM: Artificial Sequence
<220> FEATURE:
<223> OTHER INFORMATION: primer for NEUROD1

<400> SEQUENCE: 18
ctccttcgtt cagacgcttt                                               20

<210> SEQ ID NO 19
<211> LENGTH: 20
<212> TYPE: DNA
<213> ORGANISM: Artificial Sequence
<220> FEATURE:
<223> OTHER INFORMATION: primer for INS

<400> SEQUENCE: 19
catcagaaga ggccatcaag                                               20

<210> SEQ ID NO 20
<211> LENGTH: 20
<212> TYPE: DNA
<213> ORGANISM: Artificial Sequence
<220> FEATURE:
<223> OTHER INFORMATION: primer for GCG

<400> SEQUENCE: 20
cagaagaggt cgccattgtt                                               20

<210> SEQ ID NO 21
```

```
<211> LENGTH: 20
<212> TYPE: DNA
<213> ORGANISM: Artificial Sequence
<220> FEATURE:
<223> OTHER INFORMATION: primer for SST

<400> SEQUENCE: 21
ccaaccagac ggagaatgat                                                   20

<210> SEQ ID NO 22
<211> LENGTH: 20
<212> TYPE: DNA
<213> ORGANISM: Artificial Sequence
<220> FEATURE:
<223> OTHER INFORMATION: primer for PPY

<400> SEQUENCE: 22
tgcccattta ctctggactc                                                   20

<210> SEQ ID NO 23
<211> LENGTH: 20
<212> TYPE: DNA
<213> ORGANISM: Artificial Sequence
<220> FEATURE:
<223> OTHER INFORMATION: primer for AMY

<400> SEQUENCE: 23
attcgcaagt ggaatggaga                                                   20

<210> SEQ ID NO 24
<211> LENGTH: 22
<212> TYPE: DNA
<213> ORGANISM: Artificial Sequence
<220> FEATURE:
<223> OTHER INFORMATION: primer for ISL1

<400> SEQUENCE: 24
atttccctat gtgttggttg cg                                                22

<210> SEQ ID NO 25
<211> LENGTH: 20
<212> TYPE: DNA
<213> ORGANISM: Artificial Sequence
<220> FEATURE:
<223> OTHER INFORMATION: primer for MAF-A

<400> SEQUENCE: 25
ttcagcaagg aggaggtcat                                                   20

<210> SEQ ID NO 26
<211> LENGTH: 20
<212> TYPE: DNA
<213> ORGANISM: Artificial Sequence
<220> FEATURE:
<223> OTHER INFORMATION: primer for GCK

<400> SEQUENCE: 26
ggagagaaag cgctgaggac                                                   20

<210> SEQ ID NO 27
<211> LENGTH: 20
<212> TYPE: DNA
<213> ORGANISM: Artificial Sequence
<220> FEATURE:
<223> OTHER INFORMATION: primer for UCN3

<400> SEQUENCE: 27
```

```
gagggaagtc cactctcggg                                               20

<210> SEQ ID NO 28
<211> LENGTH: 20
<212> TYPE: DNA
<213> ORGANISM: Artificial Sequence
<220> FEATURE:
<223> OTHER INFORMATION: primer for IAPP

<400> SEQUENCE: 28
aggcagatca caaggtcagg                                               20

<210> SEQ ID NO 29
<211> LENGTH: 20
<212> TYPE: DNA
<213> ORGANISM: Artificial Sequence
<220> FEATURE:
<223> OTHER INFORMATION: primer for SLC30A8

<400> SEQUENCE: 29
tgtcccagag agagaccaga                                               20

<210> SEQ ID NO 30
<211> LENGTH: 20
<212> TYPE: DNA
<213> ORGANISM: Artificial Sequence
<220> FEATURE:
<223> OTHER INFORMATION: primer for GLUT1

<400> SEQUENCE: 30
gattcccaag tgtgagtcgc                                               20

<210> SEQ ID NO 31
<211> LENGTH: 23
<212> TYPE: DNA
<213> ORGANISM: Artificial Sequence
<220> FEATURE:
<223> OTHER INFORMATION: primer for GAPDH

<400> SEQUENCE: 31
catgagtcct tccacgatac caa                                           23

<210> SEQ ID NO 32
<211> LENGTH: 20
<212> TYPE: DNA
<213> ORGANISM: Artificial Sequence
<220> FEATURE:
<223> OTHER INFORMATION: primer for OCT3/4

<400> SEQUENCE: 32
ctggttcgct ttctctttcg                                               20

<210> SEQ ID NO 33
<211> LENGTH: 20
<212> TYPE: DNA
<213> ORGANISM: Artificial Sequence
<220> FEATURE:
<223> OTHER INFORMATION: primer for CER1

<400> SEQUENCE: 33
aaaatgaaca gacccgcatt                                               20

<210> SEQ ID NO 34
<211> LENGTH: 18
<212> TYPE: DNA
```

```
<213> ORGANISM: Artificial Sequence
<220> FEATURE:
<223> OTHER INFORMATION: primer for SOX17

<400> SEQUENCE: 34
cagcgccttc cacgactt                                                   18

<210> SEQ ID NO 35
<211> LENGTH: 22
<212> TYPE: DNA
<213> ORGANISM: Artificial Sequence
<220> FEATURE:
<223> OTHER INFORMATION: primer for FOXA2

<400> SEQUENCE: 35
cagtcgttga aggagagcga gt                                              22

<210> SEQ ID NO 36
<211> LENGTH: 20
<212> TYPE: DNA
<213> ORGANISM: Artificial Sequence
<220> FEATURE:
<223> OTHER INFORMATION: primer for HNF16

<400> SEQUENCE: 36
aggctgtgga tattcgtcaa                                                 20

<210> SEQ ID NO 37
<211> LENGTH: 22
<212> TYPE: DNA
<213> ORGANISM: Artificial Sequence
<220> FEATURE:
<223> OTHER INFORMATION: primer for HNF4a

<400> SEQUENCE: 37
ttgatgtagt cctccaagct ca                                              22

<210> SEQ ID NO 38
<211> LENGTH: 21
<212> TYPE: DNA
<213> ORGANISM: Artificial Sequence
<220> FEATURE:
<223> OTHER INFORMATION: primer for PDX1

<400> SEQUENCE: 38
attaagcatt tcccacaaac a                                               21

<210> SEQ ID NO 39
<211> LENGTH: 20
<212> TYPE: DNA
<213> ORGANISM: Artificial Sequence
<220> FEATURE:
<223> OTHER INFORMATION: primer for HNF6

<400> SEQUENCE: 39
agcttttcca ccgaggtttt                                                 20

<210> SEQ ID NO 40
<211> LENGTH: 20
<212> TYPE: DNA
<213> ORGANISM: Artificial Sequence
<220> FEATURE:
<223> OTHER INFORMATION: primer for NKX6.1

<400> SEQUENCE: 40
tcaacagctg cgtgattttc                                                 20
```

<210> SEQ ID NO 41
<211> LENGTH: 20
<212> TYPE: DNA
<213> ORGANISM: Artificial Sequence
<220> FEATURE:
<223> OTHER INFORMATION: primer for SOX9

<400> SEQUENCE: 41
agtgggtaat gcgcttggat                                          20

<210> SEQ ID NO 42
<211> LENGTH: 26
<212> TYPE: DNA
<213> ORGANISM: Artificial Sequence
<220> FEATURE:
<223> OTHER INFORMATION: primer for PROX1

<400> SEQUENCE: 42
gtaaaactca cggaaattgc taaacc                                   26

<210> SEQ ID NO 43
<211> LENGTH: 24
<212> TYPE: DNA
<213> ORGANISM: Artificial Sequence
<220> FEATURE:
<223> OTHER INFORMATION: primer for HLXB9

<400> SEQUENCE: 43
gcctttttgc tgcgtttcca tttc                                     24

<210> SEQ ID NO 44
<211> LENGTH: 20
<212> TYPE: DNA
<213> ORGANISM: Artificial Sequence
<220> FEATURE:
<223> OTHER INFORMATION: primer for CDX2

<400> SEQUENCE: 44
tcttagctgc ctttggcttc                                          20

<210> SEQ ID NO 45
<211> LENGTH: 20
<212> TYPE: DNA
<213> ORGANISM: Artificial Sequence
<220> FEATURE:
<223> OTHER INFORMATION: primer for AFP

<400> SEQUENCE: 45
tccaacaggc ctgagaaatc                                          20

<210> SEQ ID NO 46
<211> LENGTH: 20
<212> TYPE: DNA
<213> ORGANISM: Artificial Sequence
<220> FEATURE:
<223> OTHER INFORMATION: primer for NGN3

<400> SEQUENCE: 46
ctaccggcgc aaaagaatag                                          20

<210> SEQ ID NO 47
<211> LENGTH: 20
<212> TYPE: DNA
<213> ORGANISM: Artificial Sequence
<220> FEATURE:

<223> OTHER INFORMATION: primer for PAX4

<400> SEQUENCE: 47
gggtgctcat agggaaaaca                                          20

<210> SEQ ID NO 48
<211> LENGTH: 20
<212> TYPE: DNA
<213> ORGANISM: Artificial Sequence
<220> FEATURE:
<223> OTHER INFORMATION: primer for NEUROD1

<400> SEQUENCE: 48
gtggaagaca tgggagctgt                                          20

<210> SEQ ID NO 49
<211> LENGTH: 21
<212> TYPE: DNA
<213> ORGANISM: Artificial Sequence
<220> FEATURE:
<223> OTHER INFORMATION: primer for INS

<400> SEQUENCE: 49
tcttgggtgt gtagaagaag c                                        21

<210> SEQ ID NO 50
<211> LENGTH: 20
<212> TYPE: DNA
<213> ORGANISM: Artificial Sequence
<220> FEATURE:
<223> OTHER INFORMATION: primer for GCG

<400> SEQUENCE: 50
tggctagcag gtgatgttgt                                          20

<210> SEQ ID NO 51
<211> LENGTH: 20
<212> TYPE: DNA
<213> ORGANISM: Artificial Sequence
<220> FEATURE:
<223> OTHER INFORMATION: primer for SST

<400> SEQUENCE: 51
agggaagaga gatggggtgt                                          20

<210> SEQ ID NO 52
<211> LENGTH: 20
<212> TYPE: DNA
<213> ORGANISM: Artificial Sequence
<220> FEATURE:
<223> OTHER INFORMATION: primer for PPY

<400> SEQUENCE: 52
atctgctctg gtgtggcatt                                          20

<210> SEQ ID NO 53
<211> LENGTH: 20
<212> TYPE: DNA
<213> ORGANISM: Artificial Sequence
<220> FEATURE:
<223> OTHER INFORMATION: primer for AMY

<400> SEQUENCE: 53
gcccaaccca atcattaaca                                          20

```
<210> SEQ ID NO 54
<211> LENGTH: 20
<212> TYPE: DNA
<213> ORGANISM: Artificial Sequence
<220> FEATURE:
<223> OTHER INFORMATION: primer for ISL1

<400> SEQUENCE: 54
cgttcttgct gaagccgatg                                            20

<210> SEQ ID NO 55
<211> LENGTH: 20
<212> TYPE: DNA
<213> ORGANISM: Artificial Sequence
<220> FEATURE:
<223> OTHER INFORMATION: primer for MAF-A

<400> SEQUENCE: 55
cgccagcttc tcgtatttct                                            20

<210> SEQ ID NO 56
<211> LENGTH: 20
<212> TYPE: DNA
<213> ORGANISM: Artificial Sequence
<220> FEATURE:
<223> OTHER INFORMATION: primer for GCK

<400> SEQUENCE: 56
ctggtttggg gtttgaggtt                                            20

<210> SEQ ID NO 57
<211> LENGTH: 21
<212> TYPE: DNA
<213> ORGANISM: Artificial Sequence
<220> FEATURE:
<223> OTHER INFORMATION: primer for UCN3

<400> SEQUENCE: 57
tgttgaggca gctgaagatg g                                          21

<210> SEQ ID NO 58
<211> LENGTH: 19
<212> TYPE: DNA
<213> ORGANISM: Artificial Sequence
<220> FEATURE:
<223> OTHER INFORMATION: primer for IAPP

<400> SEQUENCE: 58
gtgcaatctc ggctcactg                                             19

<210> SEQ ID NO 59
<211> LENGTH: 20
<212> TYPE: DNA
<213> ORGANISM: Artificial Sequence
<220> FEATURE:
<223> OTHER INFORMATION: primer for SLC30A8

<400> SEQUENCE: 59
ccacgacctc tgcaatcatg                                            20

<210> SEQ ID NO 60
<211> LENGTH: 20
<212> TYPE: DNA
<213> ORGANISM: Artificial Sequence
<220> FEATURE:
<223> OTHER INFORMATION: primer for GLUT1
```

```
<400> SEQUENCE: 60
gacatcattg ctggctggag                                            20
```